(12) United States Patent
Sargent

(10) Patent No.: US 7,926,349 B2
(45) Date of Patent: Apr. 19, 2011

(54) DETECTION OF DEFECTS IN WELDED STRUCTURES

(75) Inventor: Jeffrey Paul Sargent, Almondsbury (GB)

(73) Assignee: BAE Systems PLC, London (GB)

( * ) Notice: Subject to any disclaimer, the term of this patent is extended or adjusted under 35 U.S.C. 154(b) by 918 days.

(21) Appl. No.: 11/662,632

(22) PCT Filed: Dec. 13, 2006

(86) PCT No.: PCT/GB2006/050449
§ 371 (c)(1),
(2), (4) Date: Mar. 13, 2007

(87) PCT Pub. No.: WO2007/068979
PCT Pub. Date: Jun. 21, 2007

(65) Prior Publication Data
US 2009/0049916 A1  Feb. 26, 2009

(30) Foreign Application Priority Data

Dec. 16, 2005  (EP) ..................................... 05270093
Dec. 16, 2005  (GB) ................................... 0525528.6

(51) Int. Cl.
*G01M 7/00* (2006.01)
(52) U.S. Cl. .......................................... 73/588; 73/645
(58) Field of Classification Search ................... 73/588, 73/596, 617, 622, 642, 644
See application file for complete search history.

(56) References Cited

U.S. PATENT DOCUMENTS

| | | | | |
|---|---|---|---|---|
| 3,916,699 A | * | 11/1975 | Moran et al. ..................... | 73/623 |
| 4,285,243 A | * | 8/1981 | Collingwood .................. | 73/623 |
| 4,581,938 A | * | 4/1986 | Wentzell ......................... | 73/623 |
| 4,593,568 A | | 6/1986 | Telford et al. | |
| 4,742,713 A | * | 5/1988 | Abe et al. ........................ | 73/620 |
| 5,161,413 A | * | 11/1992 | Junker et al. .................... | 73/634 |
| 5,285,689 A | * | 2/1994 | Hapstack et al. ............... | 73/623 |
| 6,100,711 A | * | 8/2000 | Hatley .......................... | 324/772 |
| 6,155,117 A | | 12/2000 | Stevens et al. | |
| 6,404,189 B2 | * | 6/2002 | Kwun et al. .................. | 324/220 |

(Continued)

OTHER PUBLICATIONS

Sylvie Legendre, et al., "Neural Classification of Lamb Wave Ultrasonic Weld Testing Signals Using Wavelet Coefficients", IEEE Transactions on Instrumentation and Measurement, vol. 50, No. 3, Jun. 2001, pp. 672-678.

(Continued)

*Primary Examiner* — Hezron Williams
*Assistant Examiner* — Samir M Shah
(74) *Attorney, Agent, or Firm* — Buchanan Ingersoll & Rooney PC

(57) ABSTRACT

A method of detecting defects in a welded metal structure, comprising mounting an ultrasonic transducer at or adjacent to a weld seam, and emitting ultrasonic signals so that the signals are propagated in the weld seam acting as a wave guide, and detecting reflections of the signals that may be indicative of defects in or adjacent to the weld seam. Waveguiding occurs within the weld principally because it is thicker than the plate, and thus the phase velocity in the plate is greater than that in the weld. This results in total internal reflection within the weld. In addition, an evanescent wave propagates in a region adjacent to the weld. The common problem with non destructive testing of excitation and reception of unwanted modes is greatly reduced, since it has been found that for certain frequency regions, transmitted waves will propagate only in a single mode at a predetermined frequency. As preferred the fundamental symmetric Lamb wave mode $S_0$ is employed.

37 Claims, 20 Drawing Sheets

Photograph showing the mounting of the single transducer on the edge of the steel plate.

U.S. PATENT DOCUMENTS

| | | | |
|---|---|---|---|
| 6,684,706 B2* | 2/2004 | Knight et al. | 73/623 |
| 6,888,143 B2* | 5/2005 | Vogt et al. | 250/341.1 |
| 6,959,603 B2* | 11/2005 | Knight et al. | 73/623 |
| 2002/0134178 A1* | 9/2002 | Knight et al. | 73/865.8 |
| 2004/0148730 A1* | 8/2004 | Knight et al. | 15/339 |
| 2008/0196504 A1* | 8/2008 | Johnson et al. | 73/588 |
| 2009/0000379 A1* | 1/2009 | Rath et al. | 73/592 |

OTHER PUBLICATIONS

A.A. Denisov et al., "Spot Weld Analysis With 2D Ultrasonic Arrays", Journal of Research of the National Institute of Standards and Technology, vol. 109, No. 2, Mar.-Apr. 2004, pp. 233-244.

European Search Report dated Jul. 5, 2006.

United Kingdom Search Report dated Apr. 11, 2006.

I. A. Viktorov, "Rayleigh and Lamb Waves" Plenum, 1967, Acoustic Institute, Academy of Science, pp. 1-154.

Wilcox et al., "The Effect of Dispersion on Long-Range Inspection using Ultrasonic Guided Waves" NDT&E International, 2001, vol. 34, pp. 1-9.

Wilcox et al., "An Emat Array for the Rapid Inspection of Large Structures Using Guided Waves" Review of Progress in Quantitative NDE eds. D.O. Thompson and D.E. Chimenti, A.I.P. Conference Proceedings, 2003, vol. 22, 8 pages.

Wilcox et al., "Omni-Directional Guided Wave Inspection of Large Metallic Plate Structures Using an EMAT Array" IEEE Transactions on Ultrasonics Ferroelectrics and Frequency Control, 2004, pp. 1-21.

Form PCT/ISA/210 (International Search Report) dated Mar. 13, 2007.

Form PCT/ISA/237 (Written Opinion of the International Searching Authority) dated Mar. 13, 2007.

* cited by examiner

Fig.1.

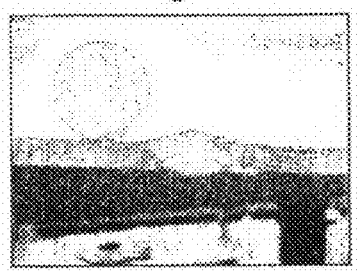

Figure 1. Weld cross-section. The plate is 6mm thick. A £1 coin is shown for size comparison.

Fig.2a.

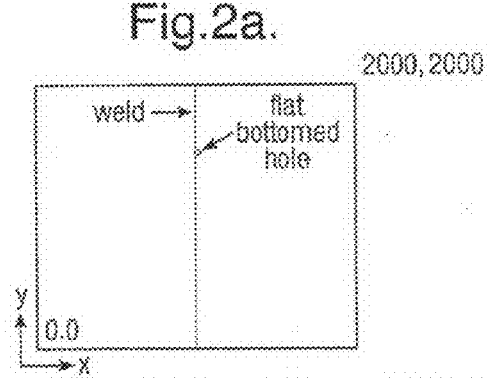

Fig.2b.

Figure 2a. Schematic diagram defining the co-ordinates and showing the location of the hole in the welded steel plate. b. Photograph of a 3mm deep 20mm diameter flat bottomed hole located adjacent to the weld.

Fig.3.

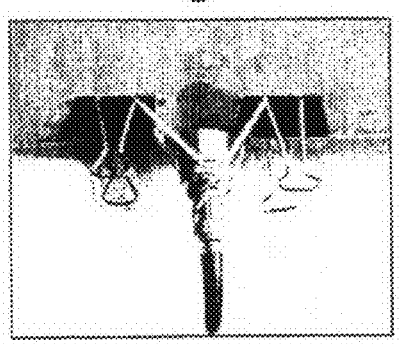

Figure 3. Photograph showing the mounting of the single transducer on the edge of the steel plate.

Figure 4a. Phase velocity calculated for a 6mm thick steel plate. b. Group velocity for 6mm thick steel plate.

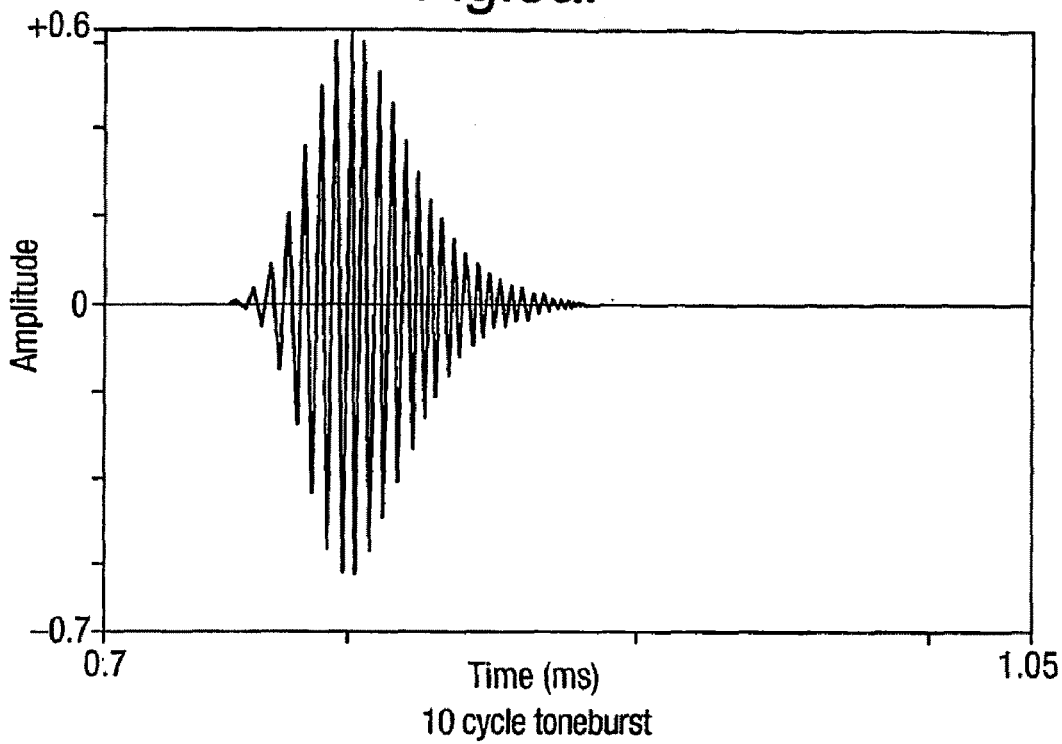
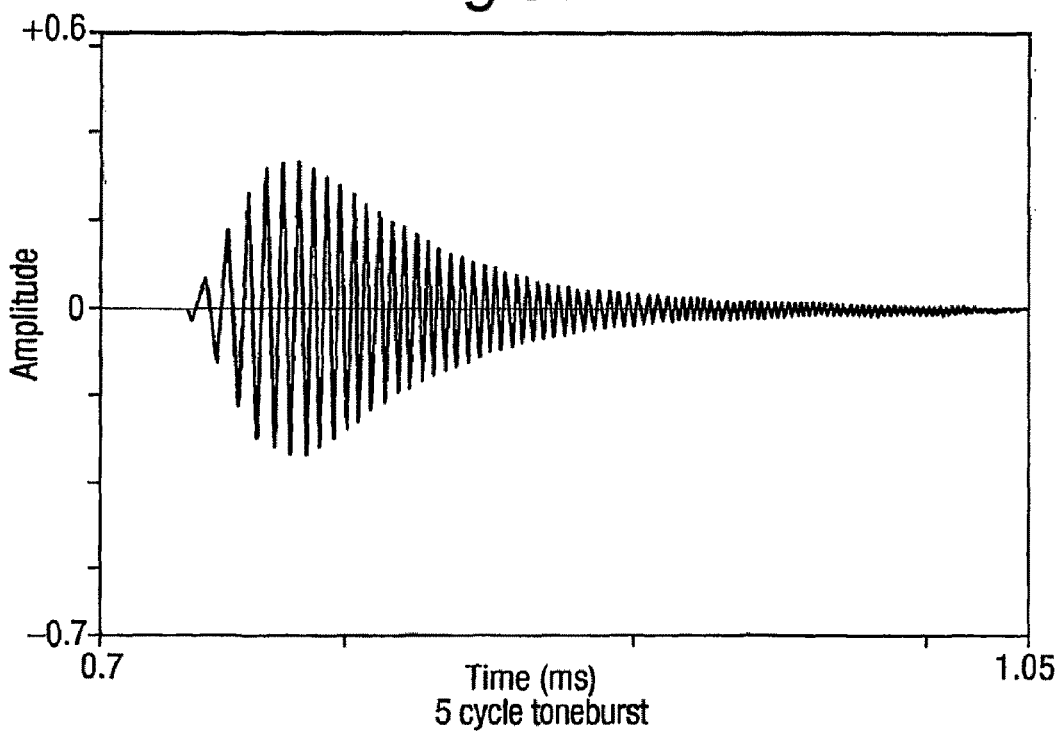
Figure 5. Predicted comparison of echoes using Disperse at 200kHz after 4m propagation (e.g. a plate edge, in pulse echo mode.)

Figure 6. Mode shapes calculated for $S_0$ mode at 200 kHz in a 6mm thick steel plate.

Figure 7. Schematic diagram defining weld location, flat bottomed hole location together with the approximate locations of the single edge mounted transducer.

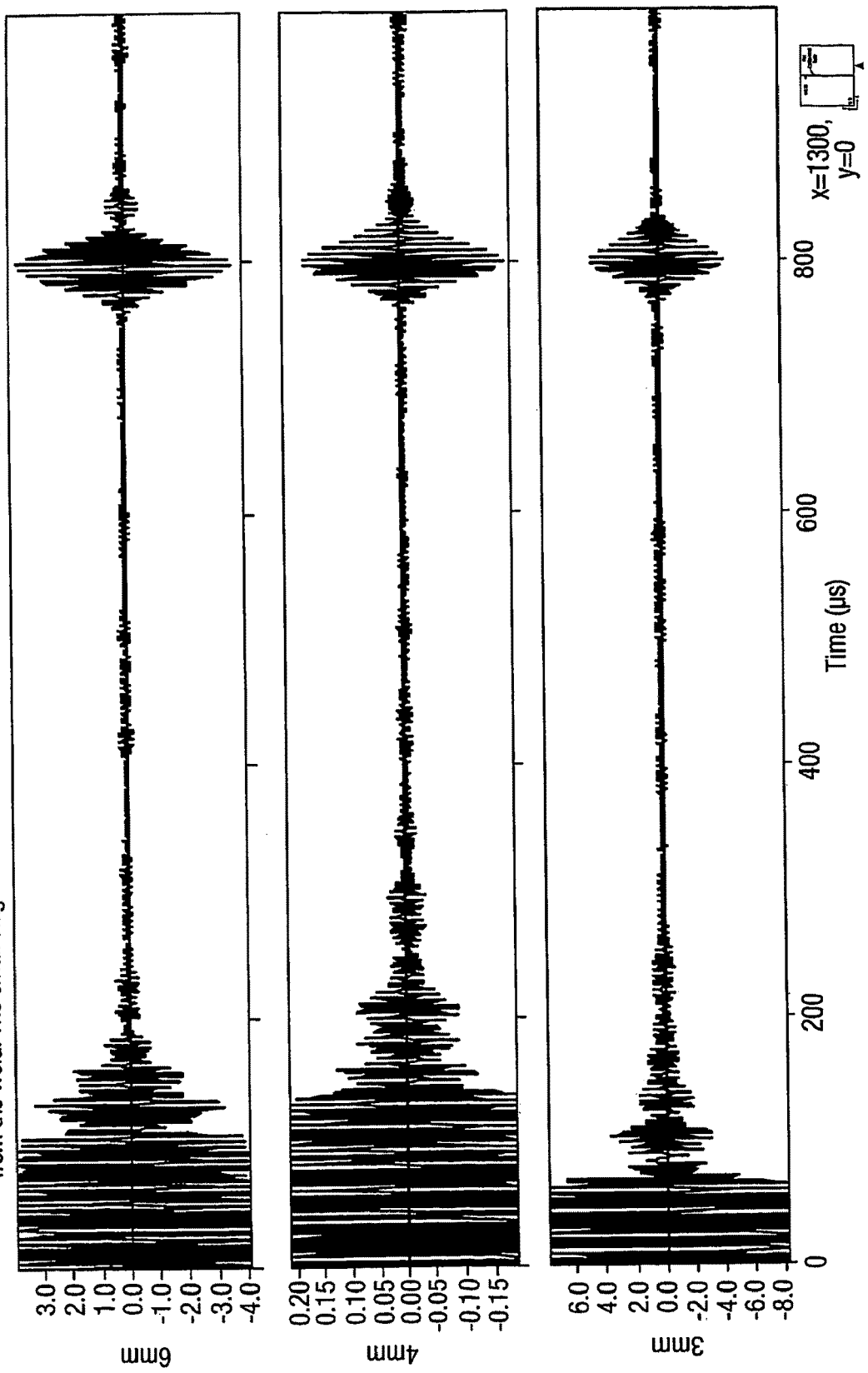
Fig. 8. Figure 8. Time traces recorded as a function of hole size for the single edge mounted transducer remote from the weld. The small diagram at the bottom shows the transducer location (black arrow). 10 Cycle tone burst, 200kHz.

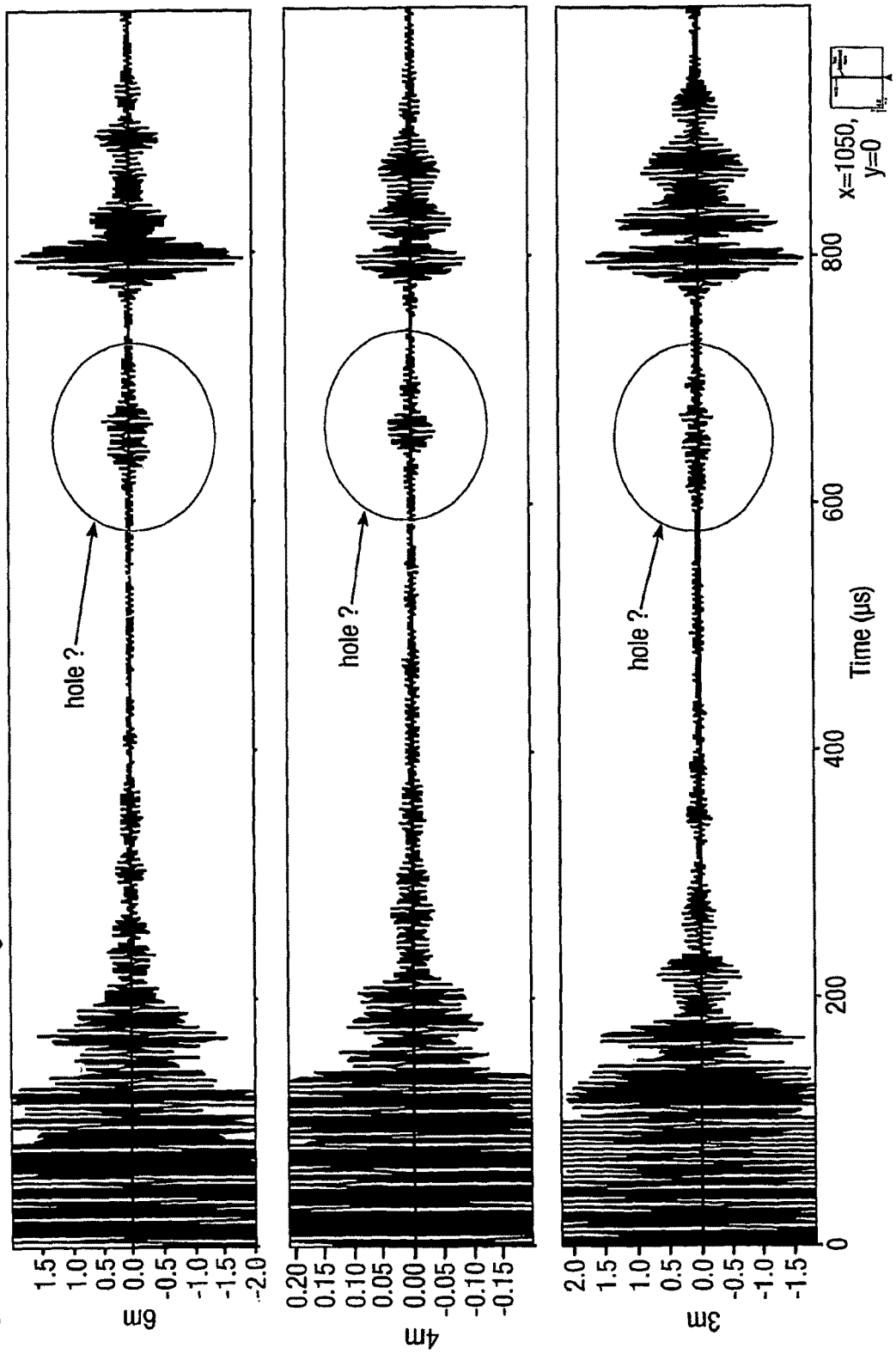

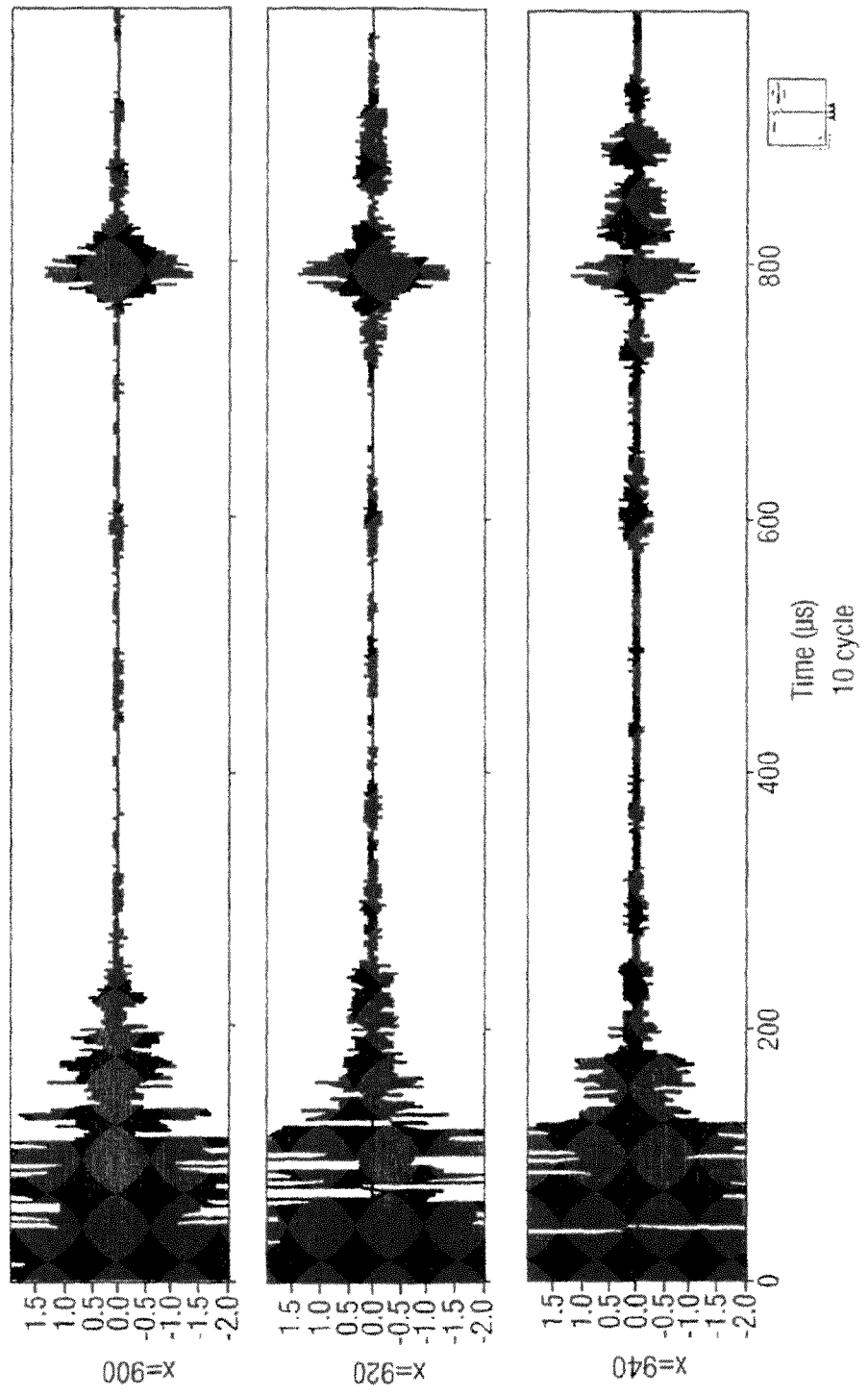

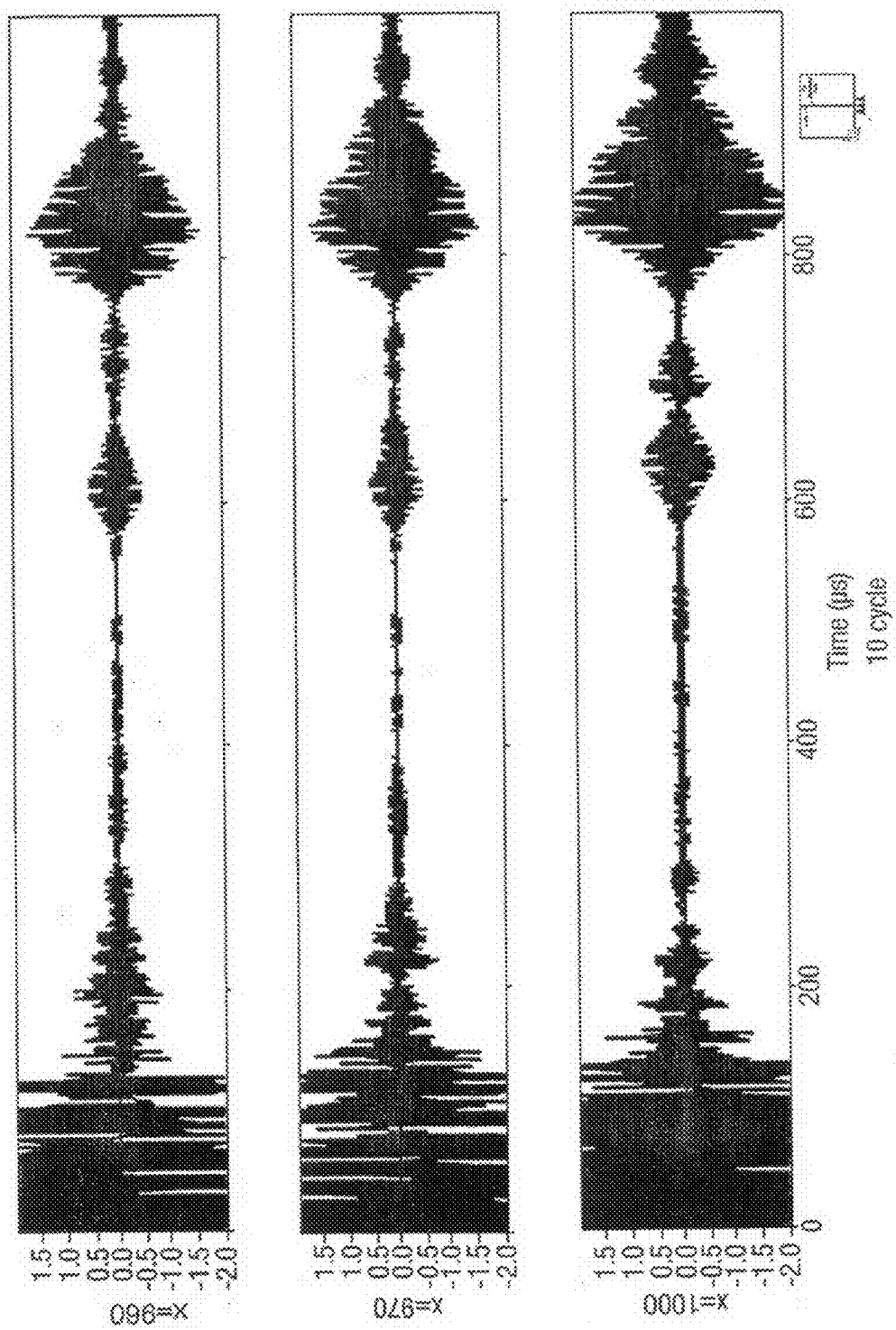

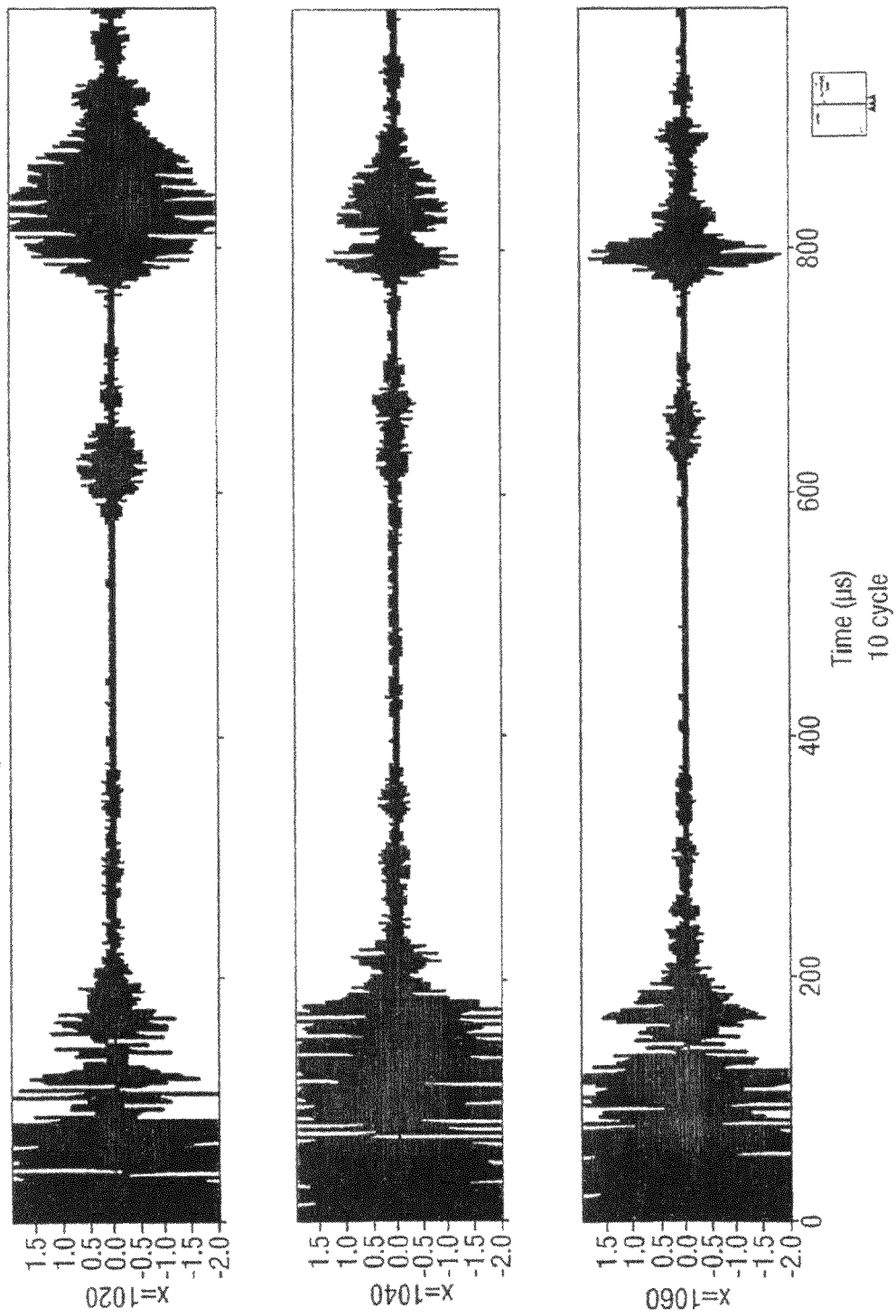
Fig.10(Cont.I).

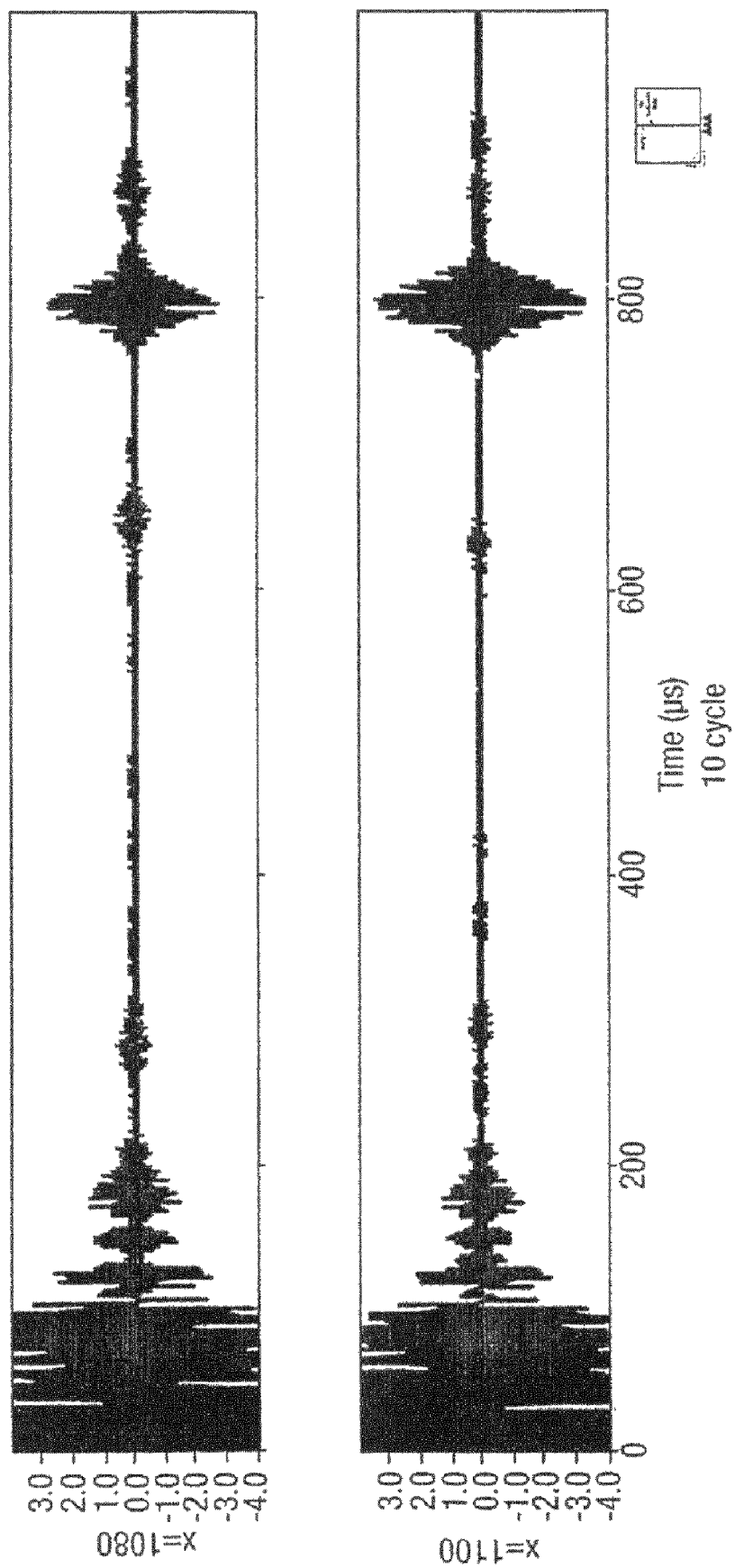

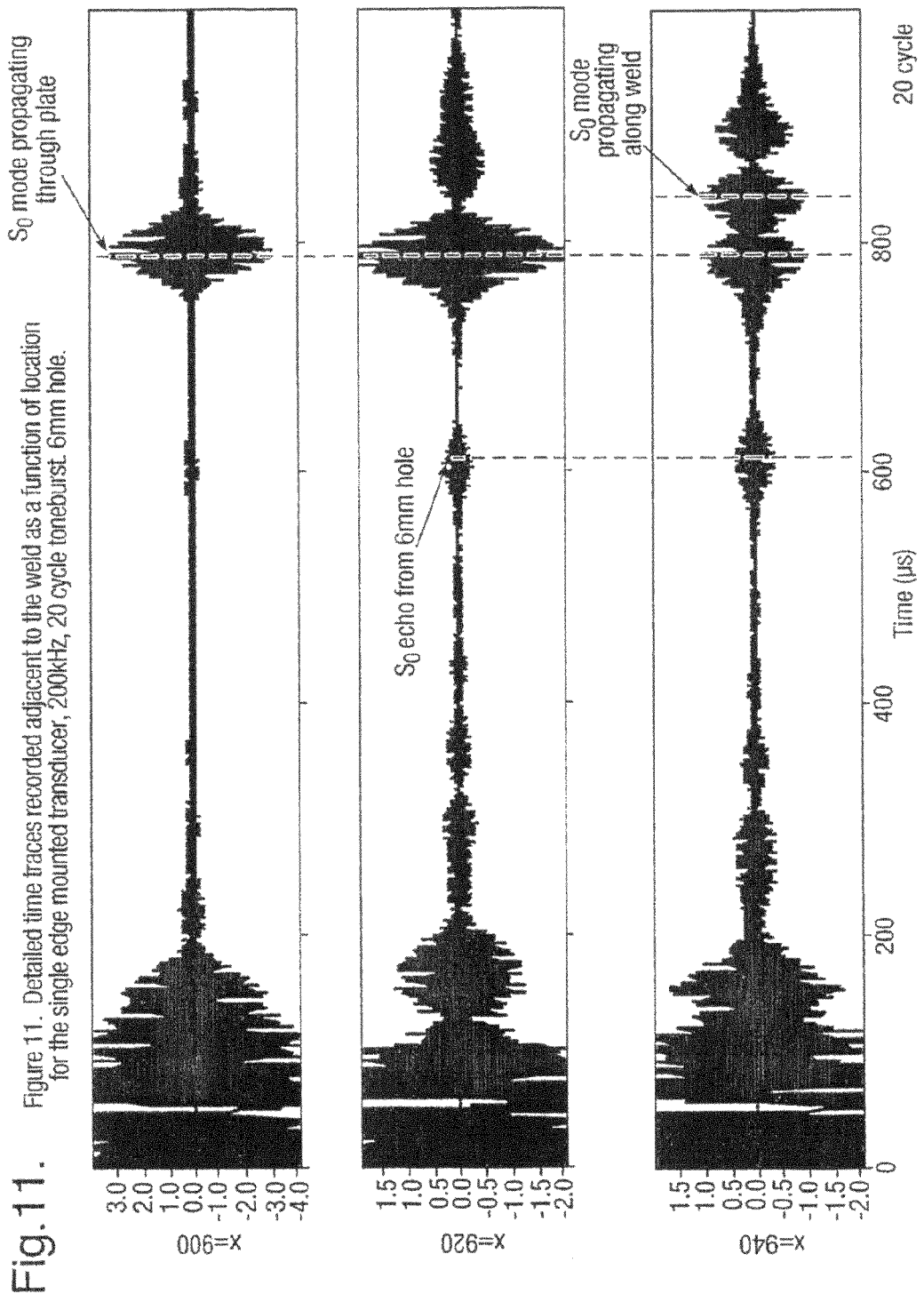
Figure 11. Detailed time traces recorded adjacent to the weld as a function of location for the single edge mounted transducer, 200kHz, 20 cycle toneburst, 6mm hole.

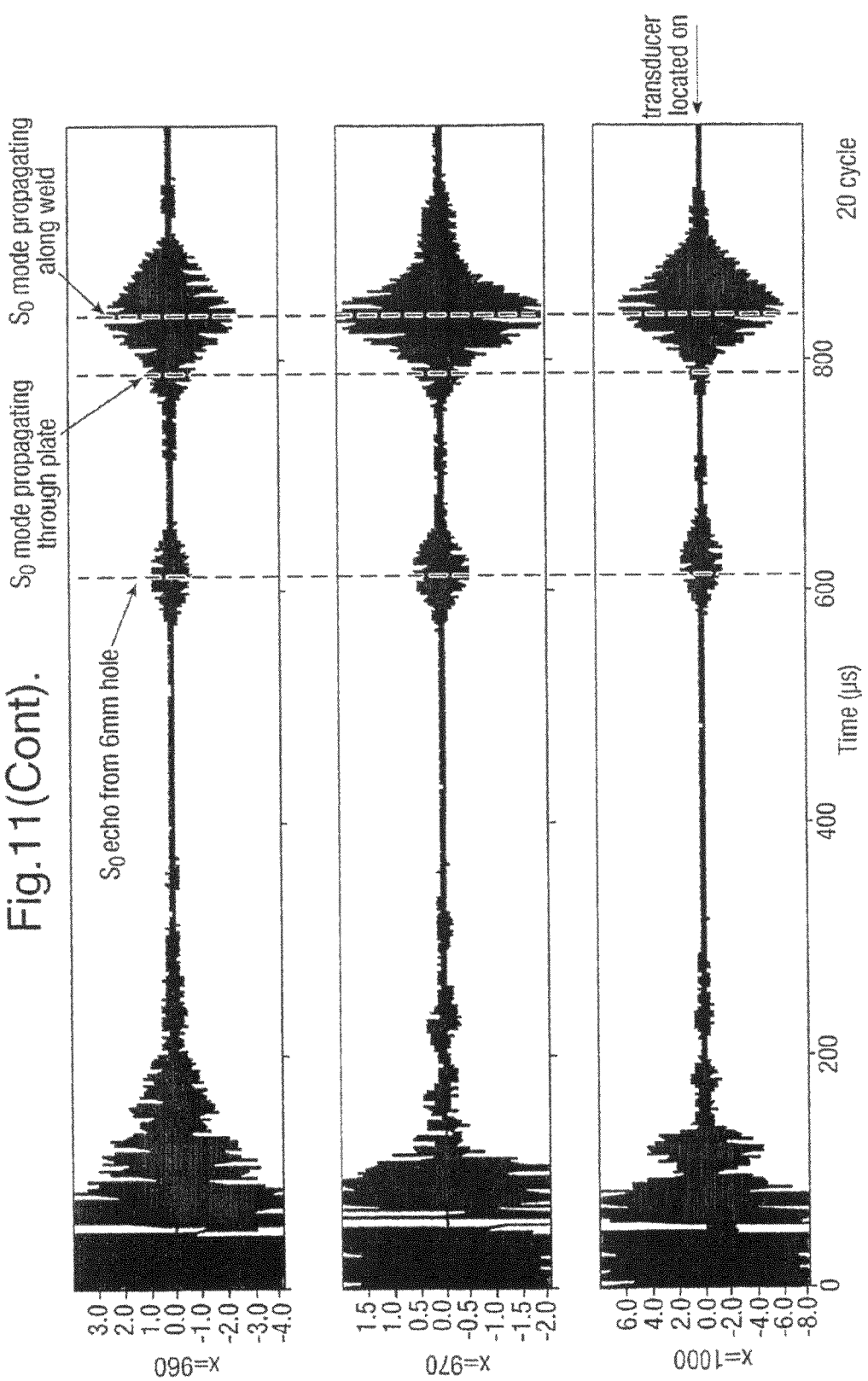

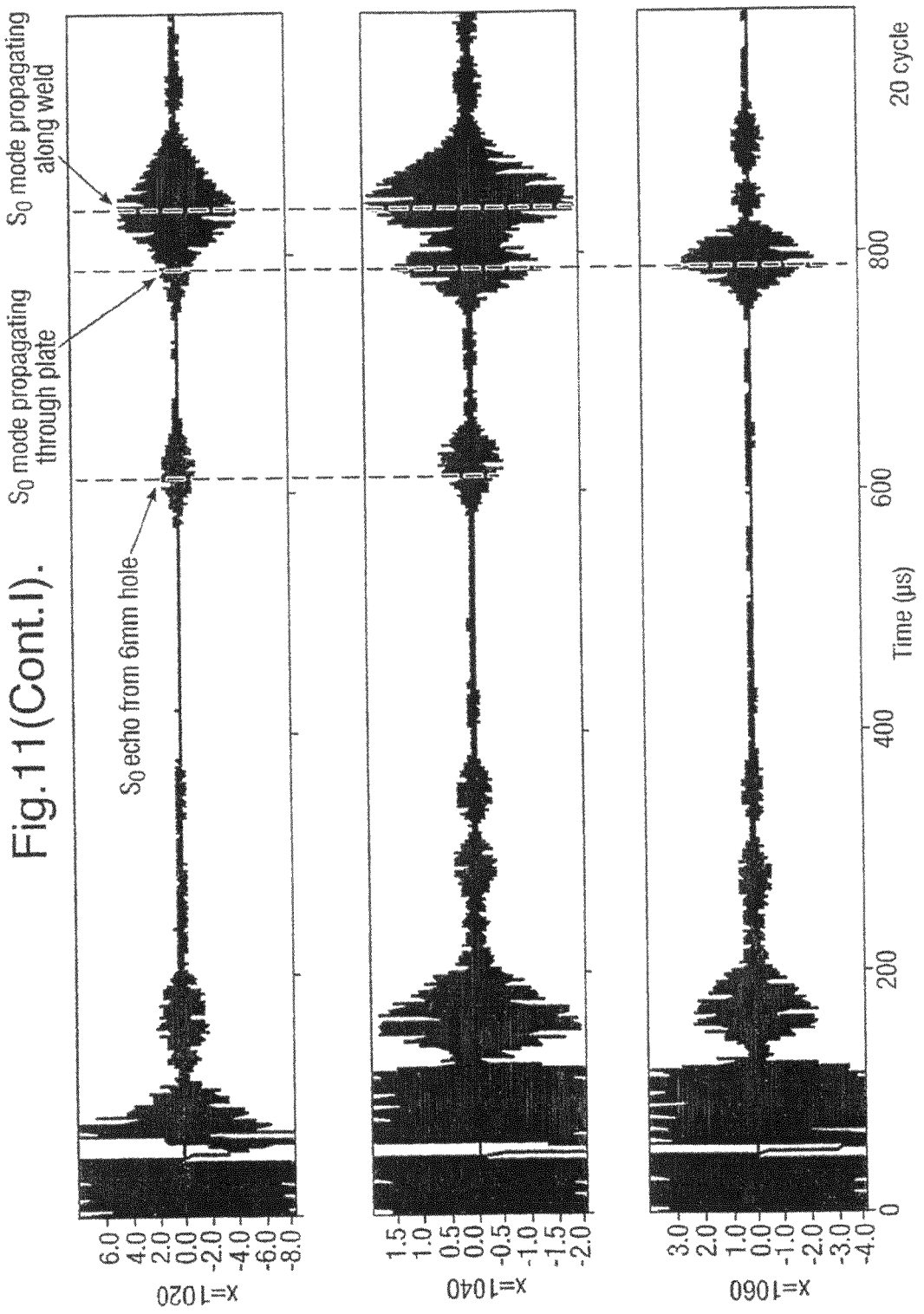
Fig. 11 (Cont.I).

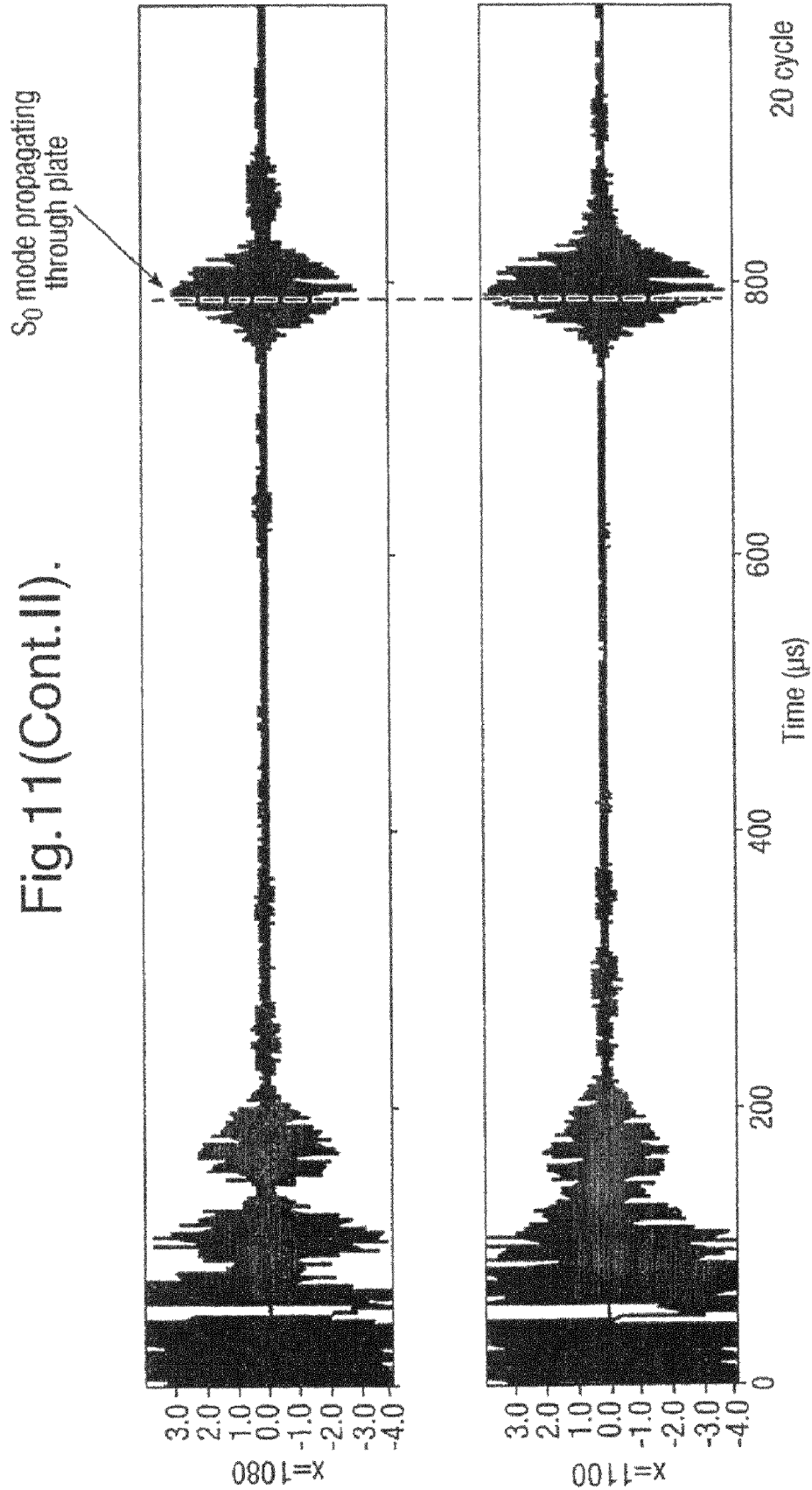

Figure 12. Detailed time trace recorded for the single edge mounted transducer located on the weld at the opposite end of the plate. 20 cycle toneburst at 200kHz. Schematic diagram shows the transducer location at x=1000 y=2000 (black arrow).

Figure 13. Schematic diagram showing the location of the new 2mm flat bottomed hole and the transducer (indicated by black arrow at x=1000 y=0).

Figure 15. Summary of reflected signals measured using the single trasducers and the plate tester. Linear fits and extrapolations are also shown to indicate likely predicted minimum detectable hole size based on the indicated coherent noise levels.

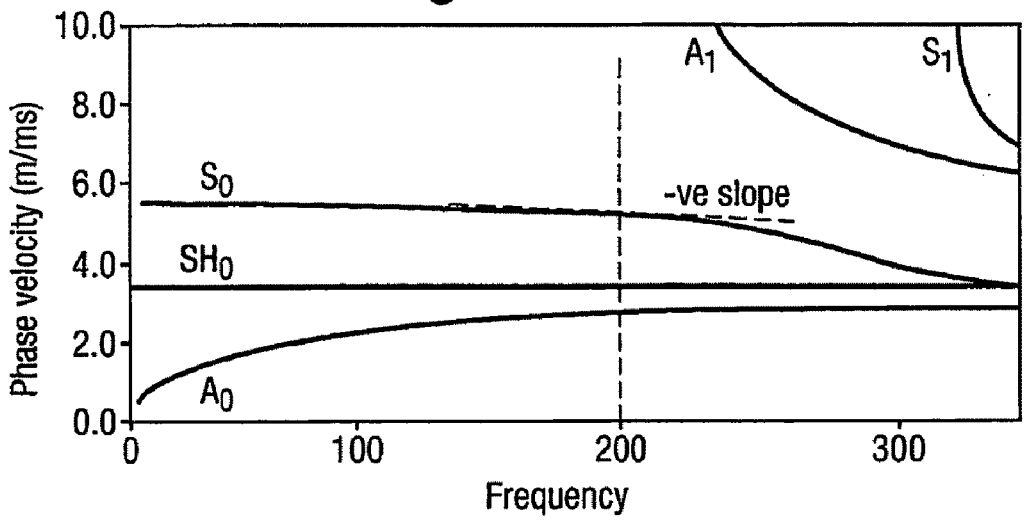
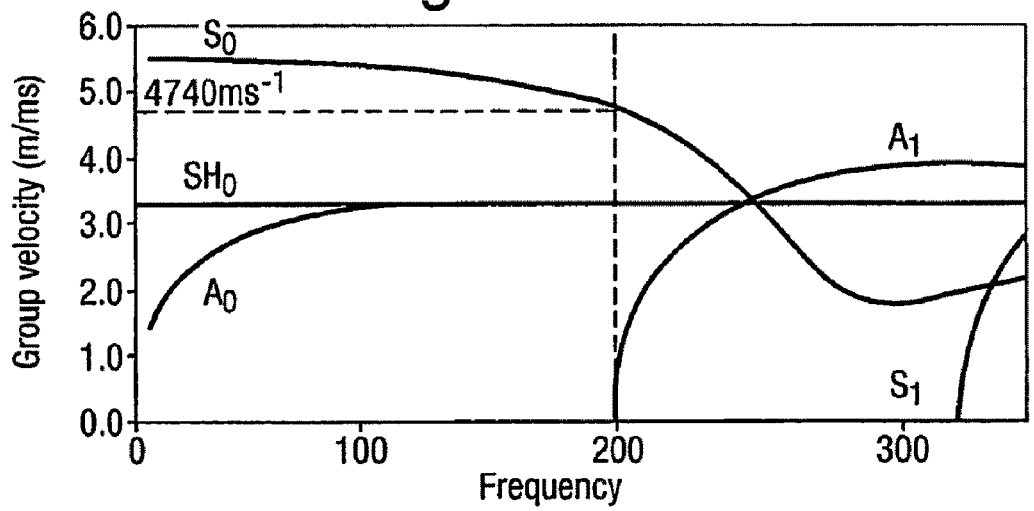
Figure 16. Dispersion curves for 8mm thick steel weld. Operating point at 200kHz is shown. a. Phase velocity, b. Group velocity.

DETECTION OF DEFECTS IN WELDED STRUCTURES

FIELD OF THE INVENTION

The present invention relates to a method and apparatus using ultrasonic waves for detection of corrosion type defects in welded structures such as tanks used for the storage of water, ballast or fuel.

BACKGROUND ART

Current methods used for inspection of storage tanks require access to their internal surfaces and a visual assessment of corrosion. This is both a time consuming and expensive procedure, requiring emptying of the tanks and inhospitable working conditions. An alternative to local inspection is to use guided waves to inspect large areas from a sensor. This approach has been used for corrosion detection in oil pipelines, and more recently in the development of methods for inspection of large areas of plates; see P Wilcox, M Lowe and P Cawley, "An EMAT array for the rapid inspection of large structures using guided waves", Review of progress in quantitative NDT, eds. D O Thompson and D E Chimenti, A.I.P. Conference Proceedings, Vol 22, 2003; P Wilcox, M Lowe and P Cawley, "Omni-directional Guided Wave Inspection of Large Metallic Plate Structures Using an EMAT Array", IEEE Transactions on Ultrasonics Ferroelectrics and Frequency Control, 2004; P Wilcox, M J S Lowe and P Cawley, "The effect of dispersion on long range inspection using ultrasonic guided waves", NDT & E International, 34, pp 1-9, 2001. The technique employed involves scanning a two dimensional plate in all directions by generating an electronically steered ultrasonic beam with an EMAT transducer of a special construction.

Ultrasonic waves employed in plates in non-destructive testing (NDT) applications are commonly Lamb waves. Lamb waves are defined and explained in Viktorov, Acoustic Institute, Academy of Sciences, USSR "Rayleigh and Lamb Waves", Plenum, 1967: "Lamb waves refer to elastic perturbations propagating in a solid plate (or layer) with free boundaries, for which displacements occur both in the direction of wave propagation and perpendicularly to the plane of the plate. Lamb waves represent one of the types of normal or plate modes in an elastic waveguide, in this case a plate with free boundaries. For this reason Lamb waves are sometimes simply called normal modes in a plate. But this definition is rather loose, insofar as another type of normal mode can exist in a plate with free boundaries, namely transverse normal modes, wherein the motion is perpendicular to the direction of propagation and parallel to the boundaries of the plate."

Analysis reveals that for wave motion perpendicular to the direction of propagation, and perpendicular to the thickness of the plate, there are two groups of waves, so-called symmetrical Lamb waves (S) and anti-symmetrical Lamb waves (A). In symmetrical waves, the motion resembles alternate expansion and contraction of the plate in the thickness direction, whereas in anti-symmetrical waves, the wave motion resembles alternate bending of the plate in opposite directions across the thickness of the plate. There exists a finite number of each type of wave, termed orders (n), with the wavelength of higher orders harmonically related to the zeroth order. The orders differ from one another by their phase and group velocities.

There are other types of wave that propagate in plates that are not usually termed Lamb Waves, for example shear (SH) or transverse waves wherein the wave motion is parallel to the plate boundaries.

Guided waves in plates will leak energy into the surrounding media if the plate is immersed in a liquid. This will be particularly marked if the media is viscous, and will occur much more where the mode type results in the surface deformation having out-of-plane motion, rather than in-plane motion. In general, this means antisymmetric Lamb wave modes have high attenuation, and symmetric Lamb Wave modes with little out-plane surface displacement will show insignificant attenuation as a result of liquid loading. However, this usually means that specialised transducers are required which are sensitive to in-plane surface displacement. Surface mounted EMATs (Electromagnetic acoustic transducers) and shear piezoelectric transducers can be used to generate and receive symmetric modes, such as the fundamental $S_0$ or $SH_o$ modes.

Complications associated with guided wave inspection arise because, in general, the waves propagate with different velocities at different frequencies (a phenomenon known as dispersion), and also because the excitation and reception of unwanted modes result in overlapping and confusing signals. Typical practical problems associated with the use of guided waves also arise from reflections from plate edges, the presence of stiffeners, the presence of welds and joints, and thickness changes.

SUMMARY OF THE INVENTION

It is commonly accepted that the weld joint is the most critical area from a performance perspective, because many detrimental features can occur; these include changes in microstructure, welding imperfections and the presence of residual stress. It is also believed that these imperfections can result in selective corrosion, either in the weld itself or in the heat affected zone (HAZ) adjacent to the weld. The present invention is directed towards the detection of corrosion in the weld or heat affected zone. In particular, given that the weld might be imperfectly finished, or that the weld might itself obscure signals originating from corroded areas, there is also implicitly the additional optional requirement to detect and discriminate reflections that originated from the weld from those originating from corrosion.

The concept of the present invention is to inject an ultrasonic wave, commonly a Lamb wave, of a predetermined mode and frequency so that it propagates along the length of a weld seam wherein the weld seam constitutes a wave guide for the ultrasonic wave. The difference in weld and plate thickness and material properties cause different propagation (phase) velocities in the weld compared with the plate and this in turn causes the weld to act as a wave guide, as described below. For the purposes of this specification, "waveguide" is intended to mean a transmission medium that confines and guides the energy of an ultrasonic wave. Confinement occurs by internal reflection of the waves at the walls at the boundaries of the waveguide. For perfect waveguide action, there is total internal reflection at the boundaries, and no escape of energy from the waveguide. However there may in practice be loss of energy from the waveguide where the internal reflection is less than total. In accordance with waveguide theory, there exists an evanescent wave extending a short distance outwardly from the boundaries of the waveguide, and this property may be exploited with the present invention as explained below.

In accordance with the invention, very small flaws in the weld and the heat affected area adjacent to the weld may be detected. Because the energy of the transmitted signal is transmitted along the weld seam, only reflections from sites within or adjacent to the weld seam will occur. Further the common problem with NDT of excitation and reception of unwanted modes is greatly reduced, since it has been found that for certain frequency regions, transmitted waves will propagate only in a single mode at a predetermined frequency.

In a first aspect, the invention provides a method of detecting defects in a welded metal structure, comprising mounting an ultrasonic transducer at or adjacent to a weld seam, and emitting ultrasonic signals that are propagated in the weld seam acting as a wave guide, and detecting reflections of the signals that may be indicative of defects within or adjacent the weld seam.

In a second aspect, the invention provides apparatus for detecting defects in a welded metal structure, comprising an ultrasonic transducer mounted at or adjacent to a weld seam, and arranged to emit ultrasonic signals that are propagated in the weld seam acting as a wave guide, and means for detecting reflections of the signals that may be indicative of defects within or adjacent the weld seam.

The transducer may be mounted on the edge of the plate in which the weld seam is located, as described hereinafter. Alternatively, the transducer may be mounted to the surface of the plate adjacent to the weld seam. The transducer may be magnetically clamped to the metal plate or mechanically clamped or otherwise secured to the plate. The transducer may be a piezoelectric transducer or an EMAT type transducer, inter-digital transducer, or other type of transducer used in non-destructive testing.

The transducer is preferably arranged both to transmit signals and to receive reflected signals. A transceiver means is coupled to the transducer element for providing signals for transmission and for processing received signals. The transmitted signal as preferred has a pulsed form so that reflections from potential defect sites may be detected as "echo" pulses. The pulsed signal is transmitted as a wave packet, with frequencies centred about a base frequency. The pulse is shaped so as to reduce the bandwidth, for example by means of a Hanning window (raised cosine function), so as to reduce dispersion of the pulse and because higher frequencies may occur in regions where the weld seam does not operate in a desired way. As preferred and as described below, the pulse takes the form of a tone burst defined within a Hanning window, between 5 and 20 cycles long. The longer the tone burst, the more it is monochromatic and therefore less liable to dispersion. However there may be more difficulty in discriminating reflections with a longer pulse. Other forms of window may be employed for reducing bandwidth, and they will be well known to those skilled in the art.

It has been found that, in accordance with the invention, for certain frequency regions, transmitted waves will propagate only in a single mode within the weld seam. It is therefore desirable to determine in advance, by observation or calculation, the appropriate mode of the ultrasonic wave, whether it is symmetric (S), anti-symmetric (A), shear wave (SH) or other mode, the order of the mode (denoted by subscript), and the frequency of operation in which the weld seam will act as a wave guide. It has been found, fortuitously that an appropriate mode is the fundamental symmetric mode ($S_0$) of a Lamb wave, as is described below, since this may be generated within a frequency region where other modes cannot propagate within a weld seam.

Waveguiding occurs within the weld principally because it is thicker than the plate, and thus the phase velocity in the plate is greater than that in the weld. This results in total internal reflection within the weld, in a manner analogous to that found in optical waveguides. In addition, an evanescent wave propagates in a region adjacent to the weld, with an amplitude that decays exponentially with distance from the weld, with a characteristic distance determined by the wavelength. The effectiveness with which the wave is guided will depend partly upon the extent to which the velocity in the plate is greater than that in the weld, as determined by the thickness, modulus and density difference, and partly on the monochromaticity of the wavepacket; this is explained in more detail below.

The presence of an evanescent wave existing outside of the waveguide weld seam implies that it is possible to detect defects that may exist where the strength of the evanescent wave is appreciable. Further it may be possible to site the transducer within the evanescent wave region outside of the waveguide, and still couple energy into the waveguide. In general, the useful region for an evanescent wave is one wavelength of the ultrasonic wave (say 50 mm) from the waveguide boundary, since this is where the strength of the wave is reduced by a factor of 1/e. However if a great amount of power is employed to excite the ultrasonic waves, such useful region may be extended.

Because the energy of the transmitted signal is transmitted through the weld seam, only reflections from sites within or adjacent to the weld seam will occur. Further the common problem with NDT of excitation and reception of unwanted modes is greatly reduced, since it has been found that for certain frequency regions, transmitted waves will propagate only in a single mode at a predetermined frequency. This implies that the amount of filtering and other processing of received signals may be reduced, and the overall reception process is simplified.

BRIEF DESCRIPTION OF THE DRAWINGS

A preferred embodiment of the invention will now be described with reference to the accompanying drawings wherein:

FIG. 1 is an example weld cross-section between two metal plates. The plate is 6 mm thick. A £1 coin is shown for size comparison.

FIG. 2a) is a schematic diagram defining the co-ordinates and showing the location of an example hole defect in the welded steel plate. b) Photograph of a 3 mm deep 20 mm diameter flat bottomed hole defect located adjacent to the weld.

FIG. 3 is a photograph showing the mounting of a single transducer on the edge of a steel plate.

FIG. 5 shows Predicted comparison of echoes of 5 and 10 cycle tonebursts at 200 kHz after 4 m propagation (e.g. a plate edge, in pulse echo mode).

FIG. 10 shows more detailed time traces recorded adjacent to the weld as a function of location for the single edge mounted transducer generating a 200 kHz, 10 cycle toneburst. The small schematic diagram shows an example of the transducer locations (red arrows). x=1000 defines the weld location. 6 mm hole.

FIG. 11 shows detailed time traces recorded adjacent to the weld as a function of location for the single edge mounted transducer generating 200 kHz, 20 cycle toneburst. 6 mm hole—otherwise the set up is similar to that of FIG. 10

FIG. 16 shows dispersion curves for a 8 mm thick steel weld as used in this EXAMPLE. Operating point at 200 kHz is shown. a) Phase velocity, b) Group velocity.

DESCRIPTION OF THE PREFERRED EMBODIMENT

Figure 4A:
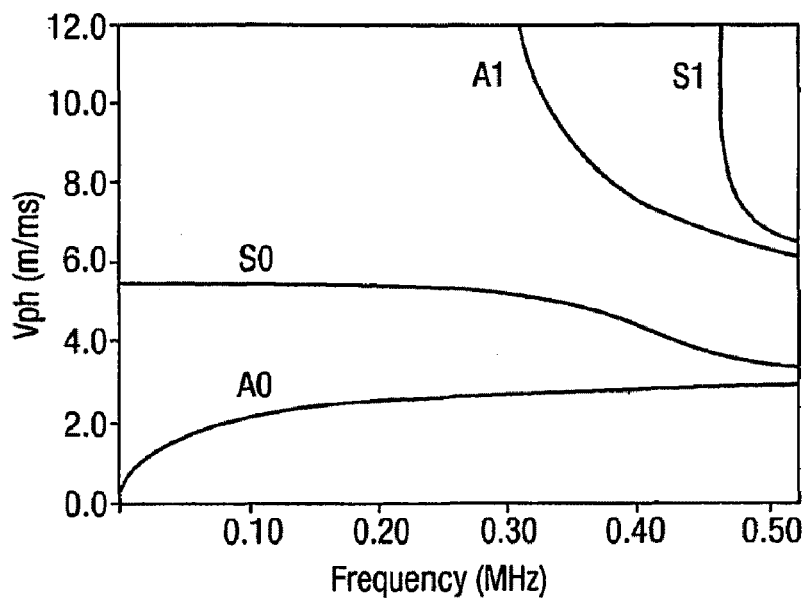
FIG. 4a) shows Phase velocity calculated for a 6 mm thick steel plate. b) Group velocity for 6 mm thick steel plate.

In a preferred embodiment, a $S_0$ Lamb wave mode is naturally guided along a weld seam acting as a waveguide, providing a very sensitive method for detection of corrosion type defects in the weld, or in the heat affected zone adjacent to the weld. The EXAMPLE described below has demonstrated a waveguide mode of operation in which an fundamental symmetric ($S_0$) Lamb wave propagates along the weld. This mode was generated using an immersion transducer edge mounted to the plate. Results may be summarised as follows:

Easy detection of a 2 mm deep, 20 mm diameter flat bottomed hole, representing a weld defect, at a distance of 1 meter was possible when using a damped transducer, 20 cycle excitation, and a frequency of 161 kHz. Based on these results, it was predicted that the minimum depth detectable for a 20 mm diameter flat bottomed hole was probably about 0.3 mm. This represents about 5% of the plate thickness. This sensitivity was achieved because of the low coherent background noise level and the waveguide nature of operation. Therefore very small defects caused by corrosion, weld imperfections etc, may be detected.

A low attenuation coefficient was measured for propagation within the waveguide. This implied that detection should be possible over many meters.

Because the $S_0$ mode is preferentially guided in the weld, interference from other modes such as fundamental antisymmetric and shear modes $A_0$ and $SH_0$ is likely to be small. This gives rise to a low coherent background noise level.

Excitation of the waveguide mode was possible either via the weld region itself, or in regions ~$\lambda$ (about the distance of one wavelength—about 50 mm) distance away, by reason of the evanescent wave existing outside the weld seam Defect detection may be limited to the weld and heat affected zone to distances ~$\lambda$ away from the weld, by reason of the evanescent wave existing outside the weld seam. At 200 kHz this is likely to be distance ~50 mm.

The EXAMPLE described here assesses the ability to discriminate and detect a corrosion-like defect, in a weld region using $S_0$ Lamb waves. Initial non-optimised measurements with a single edge mounted transducer demonstrated preferential waveguide propagation of the $S_0$ mode along the weld. This arose most significantly as a result of the increased thickness of the weld relative to the surrounding plate. This mode of testing resulted in inherent spurious echo reduction with a background coherent noise level of approximately −39 dB relative to the plate edge. This permitted easy detection of a 2 mm deep, 20 mm diameter flat bottomed hole (representing a defect) at a distance of 1 meter when using 20 cycle toneburst excitation at a frequency of 161 kHz. It is predicted that the minimum depth detectable using this waveguide mode for a 20 mm diameter flat bottomed hole was probably about 0.3 mm at a distance of many meters.

EXAMPLE

A test specimen comprised two 1 m×2 m×6 mm thick DH grade steel plates butt welded together to give a finished test plate 2 m square with a weld down the middle. The plate was supplied with both sides painted and had a weld bead as shown in FIG. 1. The welding set up was laser cut plate edge, square edge, no gap, 3.2 mm diameter welding wire in vertical position, welded against a backing tile, with a heat input of 2.38 kJmm.

A flat bottomed hole 20 mm in diameter was formed at a distance of 1.5 meters from the lower edge. This was drilled using a magnetically clamped drill. Hole depths were 0.98 mm, 2.17 mm, 3.0 mm, 3.85 mm and a through thickness hole of 6 mm located in a region adjacent to the weld. The plate co-ordinates and location of the hole with respect to the weld and the plate edges is shown schematically in FIG. 2a. FIG. 2b shows a photograph of the hole located adjacent to the weld after drilling to a depth of a 3.0 mm.

The equipment required for single transducer measurements and data acquisition comprised a single element immersion transducer (an Ultran 200 kHz, or a Panametrics 100 kHz-500 kHz wide band transducer) edge mounted on the steel plate, coupled using a gel couplant. Excitation and reception was via a "Wavemaker duet" pulser receiver, with waveform display and digitisation via a LeCroy 9400 A digital storage oscilloscope. Storage of waveforms was via an IEEE interface to a separate PC using a waveform collection software package. FIG. 3 shows the transducer edge mounted to the steel plate of FIG. 1, by an exemplary mechanical clamping arrangement comprising paper clamps and a rubber band.

The phase and group velocity calculated for a 6 mm thick steel plate is shown in FIGS. 4a) and 4b) respectively. The phase velocity relates to the velocity with which planes of equal phase, crests or troughs propagate through the medium. It may be recalled that a number of waves of different frequencies, wavelengths and velocities may be superposed to form a group, which propagate with a velocity known as the group velocity. Such a group, would, of course, disperse with time because the wave velocity of each component would be different. The importance of group velocity is that this is the velocity with which energy in the wave group is transmitted, and in the application used here, represents the velocity with which recognisable "echoes" may be observed from reflections from the flat bottomed holes.

Referring now to FIG. 16, this shows dispersion curves for an 8 mm thick weld, and indicates waveguiding occurs within the weld principally because it is thicker than the plate, and thus the phase velocity in the plate is larger than that in the weld. This results in total internal reflection within the weld, in a manner analogous to that found in optical waveguides. In addition, an evanescent wave propagates in a region adjacent to the weld, with an amplitude that decays exponentially with distance from the weld, with a characteristic distance determined by the wavelength. The effectiveness with which the wave is guided will depend partly upon the extent to which the velocity in the plate is less than that in the weld, as determined by the thickness, modulus and density difference.

Figure 4B:
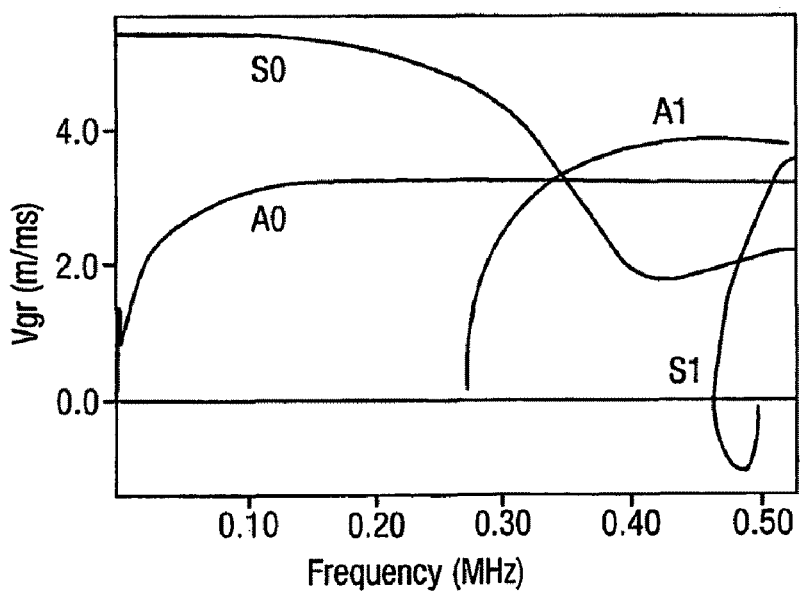

The graphs in FIG. 4 and FIG. 16 showing phase velocity versus frequency may be more generally represented as graphs of velocity versus the frequency/thickness product. So that, for example, the same point on the graph would, for example be obtained by using a frequency of 166 KHz and a thickness of 6 mm, as that for a frequency of 125 Khz and a thickness of 8 mm. Thus at the same operating frequency of say 160 KHz, this implies a frequency thickness product for the 6 mm plate of ~1 MHz-mm and ~1.3 MHz-mm for the 8 mm weld. Reading this off on the dispersion curve, this implies a larger velocity for the smaller thickness plate material than that for the weld. So a negative slope of the phase velocity curve is important in establishing that for a given frequency, then the velocity in the weld is less than in the thicker plate material.

It is also possible to envisage the opposite situation if a weld was thinner that the surrounding plate, in which case then the necessary condition would be that a positive slope in the dispersion curve is required.

The effectiveness with which the wave is guided within the weld will also depend partly on the monochromaticity of the wavepacket. Thus, for example, although greater velocity difference occurs at 200 kHz compared to 160 kHz, resulting in more effective guiding, this will be offset by the requirement for increased monochromaticity as a result of the increase in dispersion as shown on the group velocity curve at 200 kHz (see FIG. 16b). In addition, waveguide efficiency is also likely to be influenced by changes in weld geometry.

A consequence of the slopes of the phase velocity dispersion curves shown in FIG. 16a is that only $S_0$ will be guided in the weld seam in the frequency range used here. This is because the slope for $A_0$ is positive with respect to increased thickness, and that for $SH_0$ is not influenced by thickness. This effectively means that increased mode purity will result for $S_0$ as propagation occurs down the weld, with reduced influence from spurious echoes caused by the other modes $A_0$ and $SH_0$.

Figure 6:
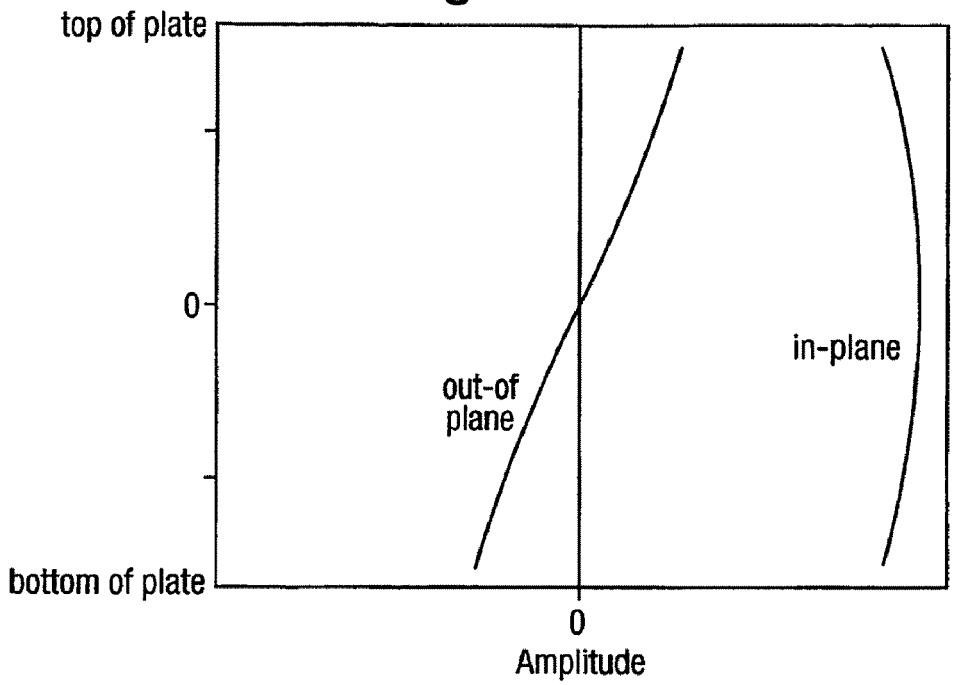
FIG. 6 shows mode shapes calculated for $S_0$ mode at 200 kHz in a 6 mm thick steel plate.

The "Wavemaker" excitation source used here was able to give Hanning windowed tonebursts comprising a user-selectable number of cycles at a particular frequency. In practice, 5, 10 or 20 cycles tonebursts at between 150 kHz and 200 kHz were used here. Noting from FIG. 4b) that the group velocity at 200 kHz for the $S_0$ mode changes quite rapidly as a function of frequency, then the shorter wavepacket, which would have a larger bandwidth, would result in greater dispersion than a longer wavepacket, which would have a smaller bandwidth, and therefore lower dispersion. An example showing the result of dispersion on both a 5 cycle and 10 cycle toneburst is shown in FIGS. 5a) and 5b) respectively for a centre frequency of 200 kHz, and a 4 m propagation distance in a steel plate (e.g. a reflected pulse from the plate edge of the 2 m square plate). There is clearly a trade-off between the desire to increase the length of pulse to prevent dispersion and the reduction in amplitude, and the requirement to keep the pulse as short as possible in order to distinguish one echo from another. In addition, shorter pulse lengths with wider bandwidth may also result in the excitation of unwanted higher order modes. Mode shapes for the $S_0$ mode at 200 kHz are shown in FIG. 6. This shows the relative amplitude for the in-plane and out-of-plane displacement for the steel plate. It may be observed that the in-plane displacement for this mode, as noted earlier, is much larger than that for the out-of-plane displacement. Therefore the $S_0$ mode is to be preferred for measurements for example in a tank where vibration may be absorbed by liquid stored within the tank.

Figure 7:
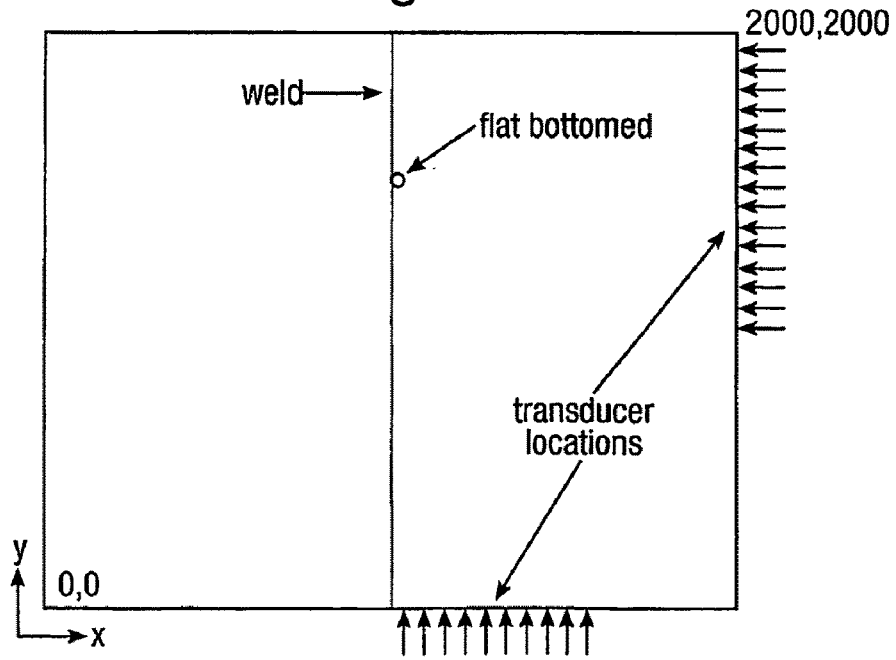
FIG. 7 is a schematic diagram of an initial test, in an EXAMPLE of the invention, defining weld location, flat bottomed hole location together with the approximate locations of the single edge mounted transducer.
Figure 8:
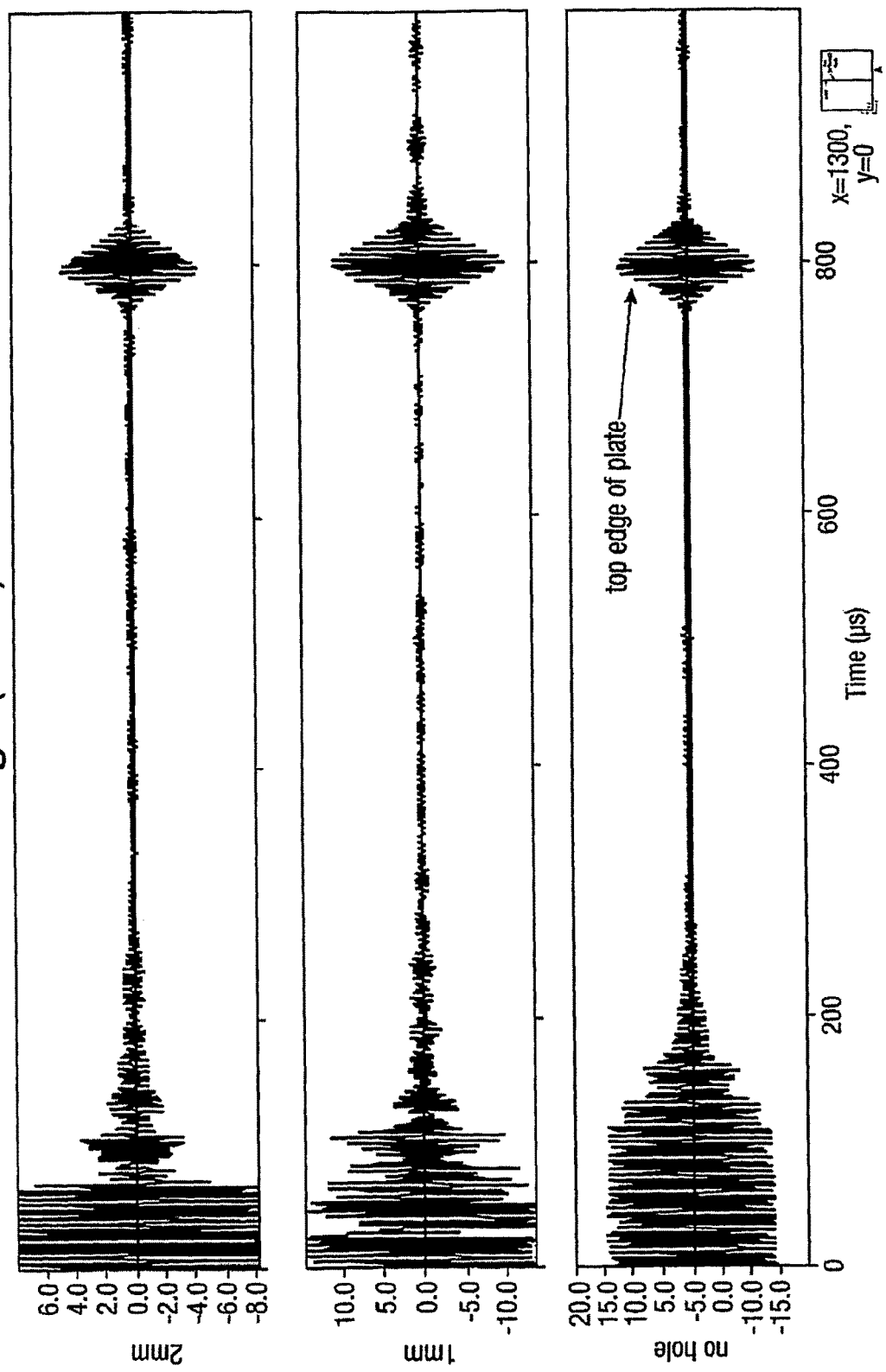
FIG. 8 shows time traces recorded as a function of hole size for the arrangement of FIG. 7, with the single edge mounted transducer remote from the weld. The small diagram at the bottom shows the transducer location (red arrow). 10 cycle toneburst, 200 kHz.

In an initial test, single pulse/echo transducer measurements at 200 kHz were made at the locations shown in FIG. 7. These were made both in the initial plate state with no hole present, and also as a function of hole size. FIG. 8 shows results of this test in the form of typical time traces recorded as a function of hole size remote from the weld region, with the transducer placed at the bottom of the plate at location x=1300, y=0, looking in a direction parallel to the weld line. The weld line is located at x=1000. The top edge of the plate, seen in FIG. 8, was clearly visible as a large reflection at a time of approximately 800 μs after the initial excitation at time t=0. Signals between time t=0 and approximately 200 μs (to the left of the image) were probably due to reverberations occurring within the probe. No signal was visible for any hole size that could be correlated with the expected position of the flat bottomed hole.

Figure 9:
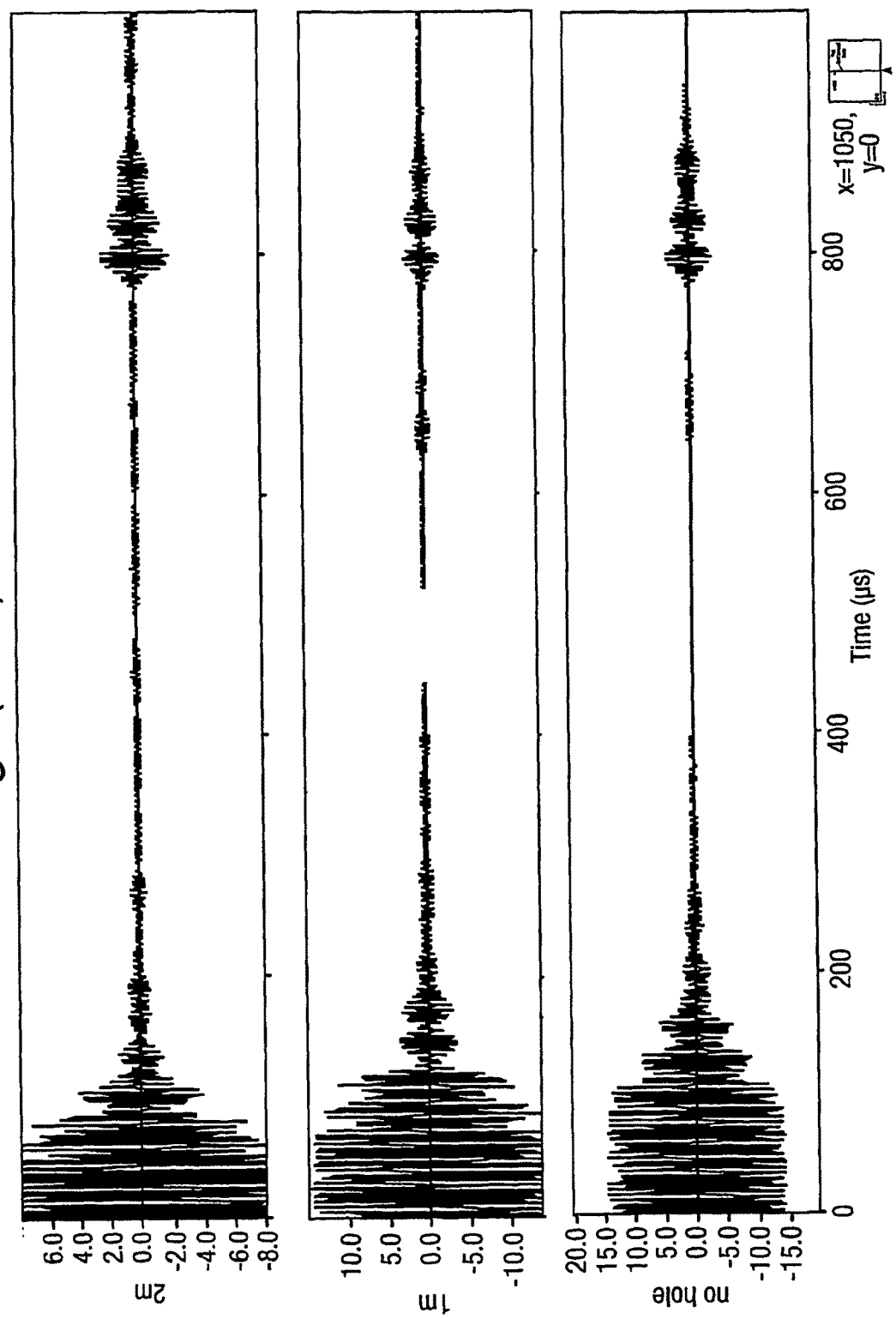
FIG. 9 shows, for a further test, time traces recorded as a function of hole size for the single edge mounted transducer near the weld. The small diagram at the bottom shows the transducer location (arrow). The transducer generates a 10 cycle toneburst at 200 kHz.

In a further test, the transducer was mounted near the end of the weld seam. The parameters of the toneburst were unchanged. The results are shown in FIG. 9. FIG. 9 shows a similar sequence of echoes as that of FIG. 8, looking in a direction parallel to the weld line, but instead recorded at a position adjacent to the weld for a location x=1050, y=0. Noteworthy differences between results from FIG. 8 and FIG. 9 were the smaller amplitude, multiple peaks, and larger time extent for reflections originating from the top plate edge, and also the appearance of reflections which appeared to be that from the flat bottomed hole, occurring at approximately 600 microseconds and before the end of plate reflections.

Since the results shown in FIG. 9 seemed to indicate fairly large signals, which appeared to indicate the presence of the hole when the transducer was located adjacent to the weld, rather than remote from the weld, a further series of more detailed results were obtained in the weld region. There was difficulty of transducer coupling in this area because the weld and adjacent plate edges was very irregular. The weld and adjacent plate edge was therefore filed sufficiently smooth to give reasonable transducer coupling and detailed results were obtained approximately 100 mm either side of the weld. FIG. 10 shows results using 10 cycle excitation at 200 kHz looking in a direction parallel to the weld, and FIG. 11 shows 20 cycle excitation, also looking in the same direction. Each time trace relates to a specific mounting of the transducer at a position denoted by the x coordinate. The weld seam is located at x=1000.

Comparison of FIGS. 10 and 11 shows lower coherent noise levels, larger signal amplitudes and easier discrimination of distinct waveform features when using 20 cycle excitation. This may be noted by comparing the 10 or 20 cycle excitation time traces for reflections from either the 6 mm hole or the rear plate edge. Inspection of FIG. 11 also shows that the 6 mm hole was clearly visible for transducer locations between about x=920, y=0 and x=1050, y=0.

Specific waveform features corresponding to the hole and plate edge are annotated in FIG. 11. In particular, this shows that the top edge plate reflection occurred at two discrete locations in the time domain, i.e. at approximately t=844 μs with propagation through the plate, and at approximately t=792 μs with propagation adjacent to the weld. The reflection from the 6 mm hole occurs at a single location of approximately t=625 μs. Noting that the total path traversed by the signal in pulse-echo mode is twice the length of the plate, i.e. 4 m, this implied velocities of approximately 5050 $ms^{-1}$ for the group plate velocity, which is consistent with the group velocity curve shown earlier in FIG. 6b for the 6 mm plate, and a velocity of approximately 4740 $ms^{-1}$ for the group velocity adjacent to the weld, implying an effective thickness of approximately 8 mm.

Noting that this thickness was close to the average thickness for the weld of about 8 mm (see FIG. 1), and that excitation of the wave with the lower velocity only occurred within ~50 mm of the weld, i.e. ~λ at this frequency, then this implied that the weld was probably acting as a waveguide. In addition, noting that the hole was located ¾ of the distance along the plate length, and noting that ¾ of 844 μs was 633 μs, i.e. approximately the time delay that was observed for the reflection from the hole, this also implied that the echo reflected from the hole was via the mode propagating along the weld waveguide. Probably the most important result to note in terms of signal to noise ratios was, however, that the amplitude of the reflected echo from the 6 mm hole was very large. If it is assumed that the hole had only a minor influence on the rear plate edge reflection, then the 6 mm hole reflection was approximately −12 dB relative to that from the rear plate edge reflection.

Figure 12:
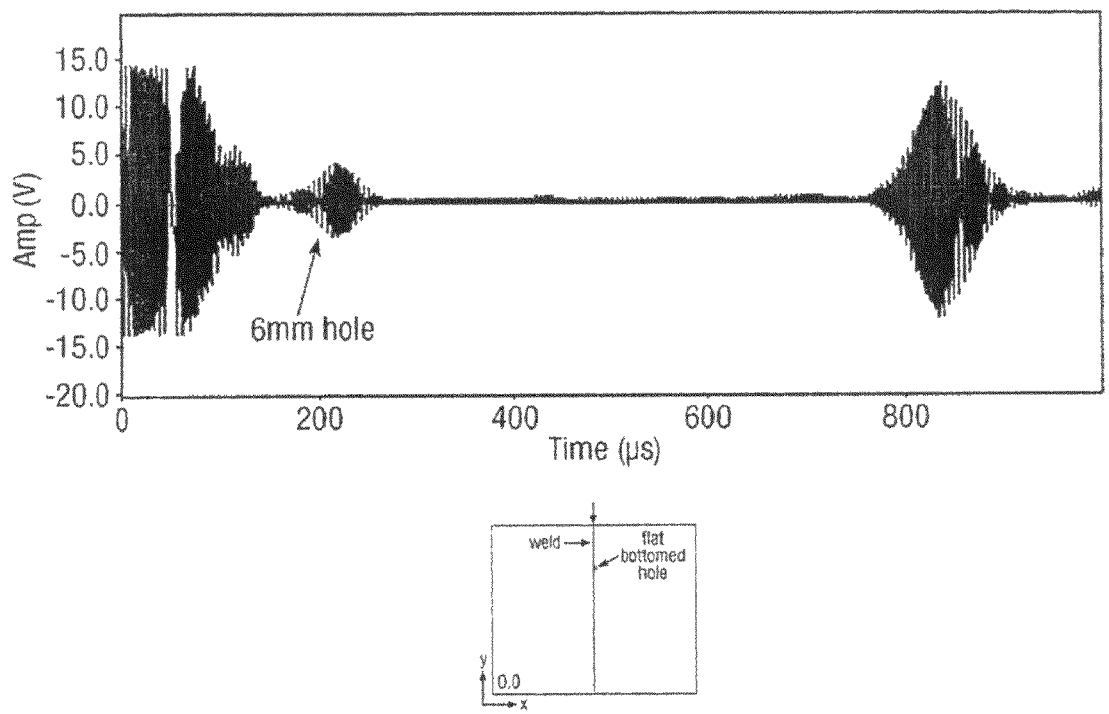
FIG. 12 is detailed time trace recorded for the single edge mounted transducer located on the weld at the opposite end of the plate—otherwise the set up is similar to that of FIG. 11 20 cycle toneburst at 200 kHz. Schematic diagram shows the transducer location at x=1000 y=2000 (arrow).

Confirmation that the reflection from the 6 mm hole originated in the fashion described was obtained by locating the transducer at the opposite end of the weld at location x=1000, y=2000. The time trace is shown in FIG. 12 for a 20 cycle excitation at 200 kHz. The 6 mm hole reflection, at an amplitude of approximately −10 dB relative to the rear plate wall reflection, is indicated in FIG. 12 and occurs at approximately 210 μs, i.e. approximately ¼ of the plate length. By noting the difference in amplitude between the ¼ distance reflection and ¾ distance reflection for the 6 mm hole, and assuming that the plate edge reflection at either end was the same, it was also possible to estimate that there was an approximate loss of only 2 dB over a total propagation distance of 2 meters.

Figure 13:
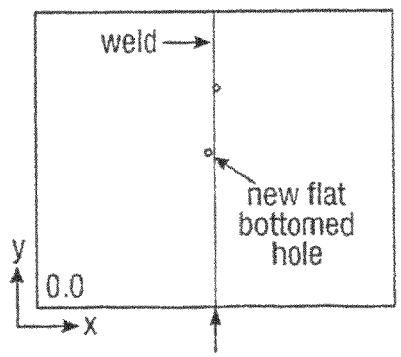
FIG. 13 is a schematic diagram showing the location of a further 2 mm flat bottomed hole and the transducer (indicated by red arrow at x=1000 y=0).
Figure 14:
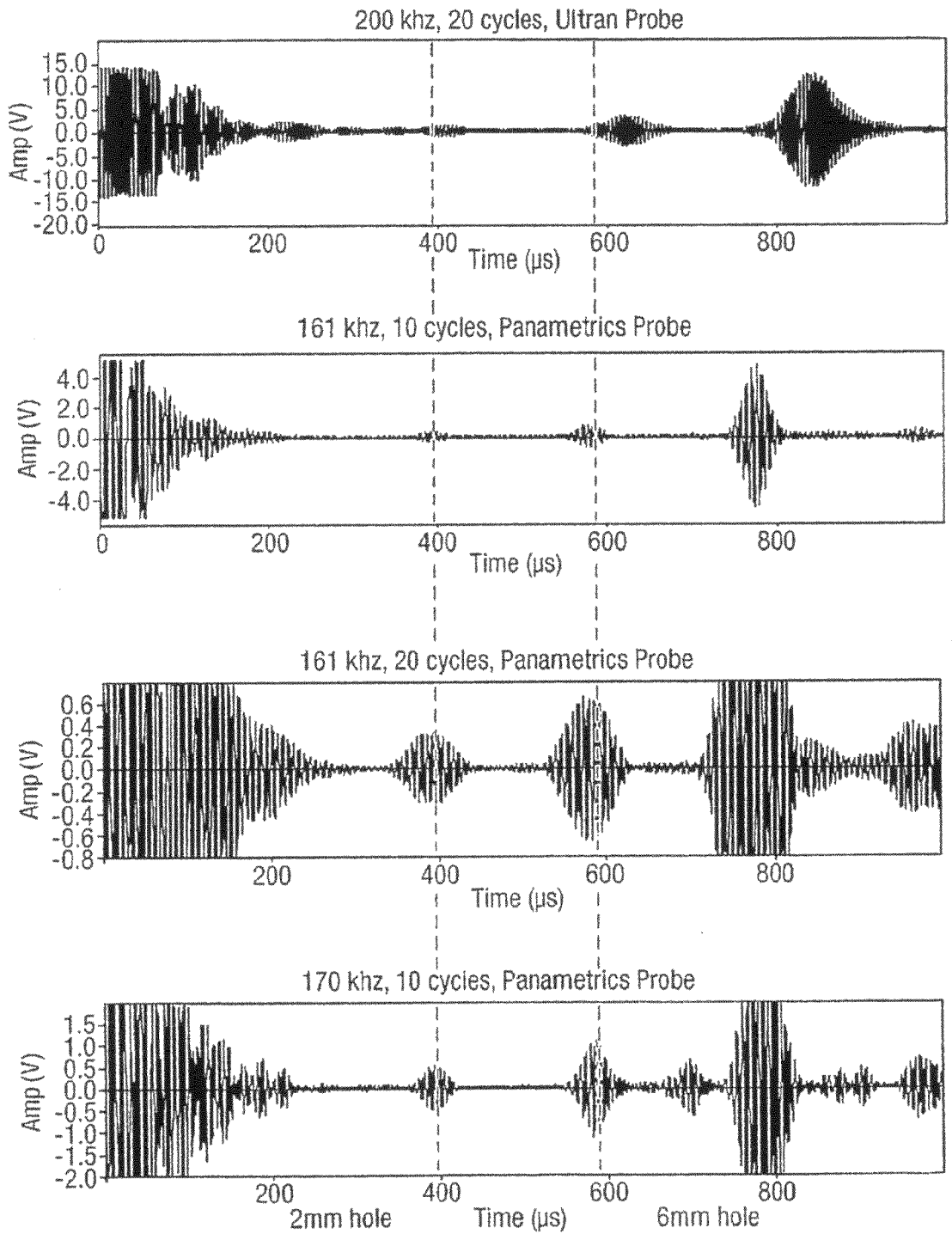
FIG. 14 shows traces, comparing use of Ultran and Panametrics transducers using various frequencies, gains and toneburst cycles. Transducers located at x=1000, y=0.
Figure 15:
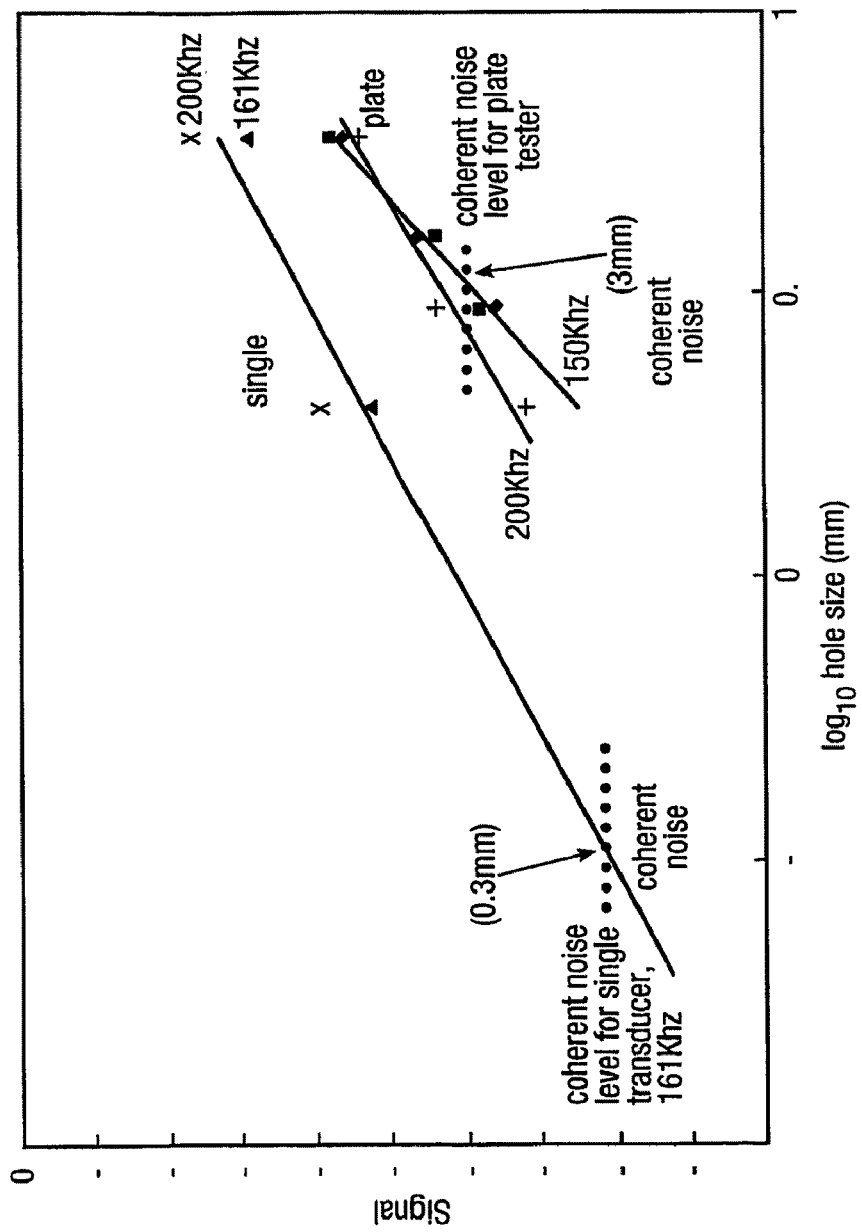
FIG. 15. Summary of reflected signals measured using a single transducer. Linear fits and extrapolations are also shown to indicate likely predicted minimum detectable hole size based on the indicated coherent noise levels.

A further 2 mm deep flat bottomed hole was drilled adjacent to the weld half way along the plate length at the location shown in FIG. 13. In addition, the opportunity was also taken to undertaken a limited study on frequency and probe optimisation when using a single edge mounted transducer. Results were obtained using both the existing 200 kHz "Ultran" transducer, and also a better damped wide band "Panametrics" transducer with a bandwidth between 100 kHz and 500 kHz. Results were obtained only when mounted on the weld at location x=1000 y=0. These are shown in FIG. 14. Inspection of FIG. 14 showed that the largest amplitude signals with least coherent noise was obtained for the Panametrics transducer at 161 kHz using 20 cycle excitation, with little evidence for any significant spurious signals occurring in the time trace up to the reflection from the rear plate edge. In this instance, if the initial transducer reverberations are discounted between time t=0 and approximately time t=300 μs, then the signal to noise ratios for both the existing Ultran transducer at 200 kHz and the Panametrics transducer at 161 kHz, using 20 cycle excitation were:
Pananametrics transducer 161 kHz, 20 cycles.
6 mm hole=−15.5 dB, 2 mm hole=−22 dB, coherent noise level=−39 dB
Ultran transducer 200 kHz, 20 cycles.
6 mm hole=−12 dB, 2 mm hole=−19 dB, coherent noise level=−30 dB These results are summarised, together with existing results from a prior art plate tester, in the graph shown in FIG. 15. Note that the single transducer signal levels for the 2 mm hole at both 161 kHz and 200 kHz have been reduced by 1 dB to give the same equivalent position as for the 6 mm hole. This adjustment was based on the loss measured above using ¼ and ¾ plate distances. FIG. 15 also shows the results of an approximate fitting of a linear regression line to an average of the 200 kHz and 161 kHz results. This has been extrapolated to give a predicted hole size based on a coherent noise level of −39 dB.

It is noteworthy that because the Panametrics probe gave no observable spurious signals and a coherent noise level of −39 dB relative to the plate edge reflection when using 20 cycle excitation at 161 kHz, then this implied a hole depth detection limit prediction of 0.3 mm (assuming the validity of the linear extrapolation as shown in FIG. 15). This would represent a detection limit of just 5% of the plate thickness.

This Example shows that a $S_0$ Lamb wave mode which is naturally guided along the weld is the most sensitive method for detection of corrosion type defects in welds with the geometry used here, or in the heat affected zone adjacent to the weld. This Example is limited to the use of flat bottomed holes as useful indicators of sensitivity to likely corrosion type defects. In practice, it is likely that real corrosion defects will deviate from this idealised geometry, and other geometries also need to be considered, for example, line type corrosion adjacent to the weld. Defect detectability for line type defects will depend on depth, subtended cross-section to the incident interrogating wave, mode type and also location with respect to other features, for example, the weld itself.

Practical design and development of a specific waveguide type transducer is considerably simplified, because the waveguide mode of operation requires no beam steering or focussing, and hence no large multi-element transducer a specific transducer will have design factors such as transducer type e.g. electromagnetic or piezo-electric excitation, transducer size, coupling and influence of paint layers and surface roughness on transduction, and, repeatability and reliability of transduction in the presence of spurious echoes.

Given that other higher order modes such as $A_1$ or $S_1$ also display a negative slope with increasing thickness in the phase velocity dispersion curves, then it is also possible that these might also serve as a useful means for detailed inspection, particularly so because of their higher frequency. In addition, although emphasis has been placed here on the use of the waveguide method for detecting corrosion in the weld and heat affected zone, the waveguide mode described here may also be suitable as an alternative to radiographic methods for inspection of the weld per se.

Single transducer excitation and reception of $S_0$ Lamb wave modes via the waveguide offered by the weld offers a very promising method for corrosion detection in the heat affected zone and for weld inspection, with the potential for the detection of small corrosion type defects and weld defects over distances of probably many meters.

Equivalents and modifications not described above may be employed without departing from the scope of the invention, which is defined in the accompanying claims.

The invention claimed is:

1. A method of detecting defects in a welded metal structure, comprising:
   mounting an ultrasonic transducer on or adjacent to a weld seam;
   emitting ultrasonic signals so that the signals are propagated in the weld seam acting as a wave guide; and
   detecting reflections of the signals that may be indicative of defects within or adjacent to the weld seam.

2. A method according to claim 1, wherein said ultrasonic signals are transmitted as waves in plate modes of vibration.

3. A method according to claim 2, wherein said transmission mode comprises a symmetric mode of a Lamb wave.

4. A method according to claim 2, wherein said transmission mode is a fundamental order of a plurality of orders of the transmission mode.

5. A method according to claim 4, wherein the pulse is shaped to reduce frequency bandwidth.

6. A method according to claim 5, wherein the pulse has the form of a Hanning Window.

7. A method according to claim 1, wherein said ultrasonic signals are transmitted in a single transmission mode.

8. A method according to claim 7, including determining in advance by calculation or observation a frequency of operation wherein the weld seam will act as a wave guide for only a single transmission mode.

9. A method according to claim 8, including determining said frequency of operation by consideration of the variation of phase velocity of the transmission modes with frequency.

10. A method according to claim 1, wherein said ultrasonic signals comprise a pulse.

11. A method according to claim 10, wherein the pulse comprises at least one toneburst between 5 and 20 cycles long.

12. A method according to claim 1, wherein said welded metal structure comprises at least one metal plate, with said weld seam extending along an edge thereof.

13. A method according to claim 12, wherein the transducer is mounted on the edge of a metal plate in which the weld seam is located.

14. A method according to claim 12, wherein the transducer is mounted to the surface of a metal plate adjacent to the weld seam.

15. A method according to claim 12, wherein the transducer is magnetically clamped or mechanically clamped to a metal plate.

16. A method according to claim 1, wherein the transducer is operative to detect received signals.

17. A method according to claim 16, including transceiver means for providing an exciting signal to the transducer, and for processing received signals therefrom.

18. A method according to claim 1, comprising locating the transducer to within about one wavelength of the ultrasonic signals to the weld seam so as to couple energy into the weld seam by reason of an evanescent wave, and to detect defects within said one wavelength.

19. A method according to claim 1, wherein the energy of the ultrasonic signals is coupled to the weld seam.

20. A method according to claim 1, wherein the weld seam confines and guides the energy of the ultrasonic signals wave.

21. Apparatus for detecting defects in a welded metal structure, comprising:
   an ultrasonic transducer mounted on or adjacent to a weld seam, and arranged to emit ultrasonic signals so that the signals are propagated in the weld seam acting as a wave guide; and
   means for detecting reflections of the signals that may be indicative of defects within or adjacent to the weld seam.

22. Apparatus according to claim 21, arranged such that said ultrasonic signals are transmitted as waves in plate modes of vibration.

23. Apparatus according to claim 21, arranged such that said ultrasonic signals are transmitted in a single transmission mode.

24. Apparatus according to claim 23, wherein said transmission mode comprises a symmetric mode of a Lamb wave.

25. Apparatus according to claim 23, wherein said transmission mode is a fundamental order of a plurality of orders of the transmission mode.

26. Apparatus according to claim 21, wherein said ultrasonic signals comprise a pulse.

27. Apparatus according to claim 26, wherein the pulse comprises at least one toneburst between 5 and 20 cycles long.

28. Apparatus according to claim 26, wherein the pulse is shaped to reduce frequency bandwidth.

29. Apparatus according to claim 28, wherein the pulse has the form of a Hanning Window.

30. Apparatus according to claim 21, wherein said welded metal structure comprises at least one metal plate, with said weld seam extending along an edge thereof.

31. Apparatus according to claim 30, including means mounting the transducer on the edge of a metal plate in which the weld seam is located.

32. Apparatus according to claim 30, including means mounting the transducer to the surface of a metal plate adjacent to the weld seam.

33. Apparatus according to claim 30, including means mounting the transducer magnetically or mechanically to a metal plate.

34. Apparatus according to claim 21, wherein the transducer is operative to detect received signals.

35. Apparatus according to claim 34, including transceiver means for providing an exciting signal to the transducer, and for processing received signals therefrom.

36. Apparatus according to claim 21, wherein the energy of the ultrasonic signals is coupled to the weld seam.

37. Apparatus according to claim 21, wherein the weld seam confines and guides the energy of the ultrasonic signals wave.

* * * * *